US012685731B2

(12) United States Patent
Li et al.

(10) Patent No.: US 12,685,731 B2
(45) Date of Patent: Jul. 21, 2026

(54) ORGANIC COMPOUNDS

(71) Applicant: INTRA-CELLULAR THERAPIES, INC., New York, NY (US)

(72) Inventors: Peng Li, New Milford, NJ (US); Robert Davis, San Diego, CA (US)

(73) Assignee: INTRA-CELLULAR THERAPIES, INC., Bedminster, NJ (US)

( * ) Notice: Subject to any disclaimer, the term of this patent is extended or adjusted under 35 U.S.C. 154(b) by 808 days.

(21) Appl. No.: 17/040,893

(22) PCT Filed: Mar. 22, 2019

(86) PCT No.: PCT/US2019/023687
§ 371 (c)(1),
(2) Date: Sep. 23, 2020

(87) PCT Pub. No.: WO2019/183546
PCT Pub. Date: Sep. 26, 2019

(65) Prior Publication Data
US 2021/0008065 A1 Jan. 14, 2021

Related U.S. Application Data

(60) Provisional application No. 62/647,482, filed on Mar. 23, 2018.

(51) Int. Cl.

| | |
|---|---|
| ***A61K 31/4985*** | (2006.01) |
| ***A61K 9/00*** | (2006.01) |
| ***A61K 45/06*** | (2006.01) |
| ***C07B 59/00*** | (2006.01) |
| ***C07D 471/16*** | (2006.01) |

(52) U.S. Cl.
CPC ........ *A61K 31/4985* (2013.01); *A61K 9/0019* (2013.01); *A61K 45/06* (2013.01); *C07B 59/002* (2013.01); *C07D 471/16* (2013.01); *C07B 2200/05* (2013.01)

(58) Field of Classification Search
CPC .. A61K 31/4985; A61K 9/0019; A61K 45/06; C07B 59/002; C07B 2200/05; C07D 471/16; C07D 471/04
See application file for complete search history.

(56) References Cited

U.S. PATENT DOCUMENTS

| | | | |
|---|---|---|---|
| 2,490,813 | A | 12/1949 | Hughes et al. |
| 3,299,078 | A | 1/1967 | Pachter |
| 3,813,392 | A | 5/1974 | Sellstedt et al. |
| 3,914,421 | A | 10/1975 | Rajagopalan |
| 4,001,263 | A | 1/1977 | Plattner et al. |
| 4,115,577 | A | 9/1978 | Rajagopalan |
| 4,136,145 | A | 1/1979 | Fuchs et al. |
| 4,155,577 | A | 5/1979 | Raymond |
| 4,183,936 | A | 1/1980 | Rajagopalan |
| 4,219,550 | A | 8/1980 | Rajagopalan |
| 4,238,607 | A | 12/1980 | Rajagopalan |
| 4,389,330 | A | 6/1983 | Tice et al. |
| 4,522,944 | A | 6/1985 | Doria et al. |
| 4,530,840 | A | 7/1985 | Tice et al. |
| 4,767,628 | A | 8/1988 | Hutchinson |
| 4,849,246 | A | 7/1989 | Schmidt |
| 4,971,971 | A | 11/1990 | Tokunaga et al. |
| 4,985,432 | A | 1/1991 | Tokunaga et al. |
| 5,004,602 | A | 4/1991 | Hutchinson |
| 5,114,976 | A | 5/1992 | Norden |
| 5,151,419 | A | 9/1992 | Perenyi et al. |
| 5,538,739 | A | 7/1996 | Bodmer et al. |
| 5,576,460 | A | 11/1996 | Buchwald et al. |
| 5,629,003 | A | 5/1997 | Horstmann et al. |
| 5,648,539 | A | 7/1997 | Goodbrand |
| 5,648,542 | A | 7/1997 | Goodbrand et al. |
| 5,654,482 | A | 8/1997 | Goodbrand |
| 5,688,801 | A | 11/1997 | Mesens et al. |
| 5,705,697 | A | 1/1998 | Goodbrand et al. |
| 5,723,669 | A | 3/1998 | Goodbrand et al. |
| 5,723,671 | A | 3/1998 | Goodbrand et al. |
| 5,763,476 | A | 6/1998 | Delbressine et al. |
| 5,770,231 | A | 6/1998 | Mesens et al. |

(Continued)

FOREIGN PATENT DOCUMENTS

| | | | |
|---|---|---|---|
| CN | 109867674 | A | 6/2019 |
| GB | 1476087 | | 6/1977 |

(Continued)

OTHER PUBLICATIONS

Saal, Pharmaceutical salts: A summary on doses of salt formers from the Orange Book, European Journal of Pharmaceutical Sciences, 2013, 49, pp. 614-623. (Year: 2013).*
Hood, Medications Used for Mental Health Illness, Understanding Pharmacology in Nursing Practice, 2020, 13, pp. 367-392 (Year: 2020).*
"Study of a Novel Antipsychotic ITI-007 in Schizophrenia," *Clinical Trials.gov*, 6 pages, Dec. 26, 2011.
Aiken, C., "An Overview of Atypical Antipsychotics for Bipolar Depression," published on Jan. 3, 2020 at https://www.psychiatrictimes.com/view/overview-atypical-antipsychotics-bipolar-depression, 11 pages.
Alvir, et al. Clozapine-Induced Agranulocytosis. The New England Journal of Medicine, 1993, vol. 329, No. 3, pp. 162-167.

(Continued)

*Primary Examiner* — Renee Claytor
*Assistant Examiner* — Andrew P Lee
(74) *Attorney, Agent, or Firm* — Hoxie & Associates LLC

(57) ABSTRACT

The invention relates to particular substituted deuterated heterocycle fused gamma-carbolines, their prodrugs, in free, solid, pharmaceutically acceptable salt and/or substantially pure form as described herein, pharmaceutical compositions thereof, and methods of use in the treatment of diseases involving 5-$HT_{2A}$ receptor, serotonin transporter (SERT) and/or pathways involving dopamine $D_1/D_2$ receptor signaling systems, and/or the treatment of residual symptoms.

15 Claims, No Drawings

(56) References Cited

U.S. PATENT DOCUMENTS

| | | | |
|---|---|---|---|
| 5,847,166 | A | 12/1998 | Buchwald et al. |
| 5,902,901 | A | 5/1999 | Goodbrand et al. |
| 5,922,338 | A | 7/1999 | Brich et al. |
| 5,922,682 | A | 7/1999 | Brich et al. |
| 5,948,430 | A | 9/1999 | Zerbe et al. |
| 5,965,168 | A | 10/1999 | Mesens et al. |
| 6,043,370 | A | 3/2000 | Kubo et al. |
| 6,110,921 | A | 8/2000 | Mesens et al. |
| 6,166,226 | A | 12/2000 | Buchwald et al. |
| 6,221,335 | B1 | 4/2001 | Foster |
| 6,235,936 | B1 | 5/2001 | Buchwald et al. |
| 6,307,087 | B1 | 10/2001 | Buchwald et al. |
| 6,323,366 | B1 | 11/2001 | Wolfe et al. |
| 6,368,632 | B1 | 4/2002 | Mesens et al. |
| 6,395,916 | B1 | 5/2002 | Buchwald et al. |
| 6,407,092 | B1 | 6/2002 | Hester et al. |
| 6,419,952 | B2 | 7/2002 | Wong et al. |
| 6,440,710 | B1 | 8/2002 | Keinan et al. |
| 6,465,693 | B2 | 10/2002 | Buchwald et al. |
| 6,541,639 | B2 | 4/2003 | Zhou et al. |
| 6,544,559 | B2 | 4/2003 | Mesens et al. |
| 6,548,493 | B1 | 4/2003 | Robichaud et al. |
| 6,552,017 | B1 | 4/2003 | Robichaud et al. |
| 6,552,024 | B1 | 4/2003 | Chen et al. |
| 6,579,881 | B2 | 6/2003 | Kitazawa et al. |
| 6,603,008 | B1 | 8/2003 | Ando et al. |
| 6,699,852 | B2 | 3/2004 | Robichaud et al. |
| 6,713,471 | B1 | 3/2004 | Robichaud et al. |
| 6,759,554 | B2 | 7/2004 | Buchwald et al. |
| 6,762,329 | B2 | 7/2004 | Marcoux et al. |
| 6,803,055 | B2 | 10/2004 | Mesens et al. |
| 6,828,314 | B2 | 12/2004 | Frank et al. |
| 6,849,619 | B2 | 2/2005 | Robichaud et al. |
| 6,849,640 | B2 | 2/2005 | Ennis et al. |
| 6,867,298 | B2 | 3/2005 | Buchwald et al. |
| 6,884,429 | B2 | 4/2005 | Koziak et al. |
| 6,888,032 | B2 | 5/2005 | Buchwald et al. |
| 6,929,803 | B2 | 8/2005 | Wong et al. |
| 6,946,560 | B2 | 9/2005 | Buchwald et al. |
| 7,026,498 | B2 | 4/2006 | Buchwald et al. |
| 7,071,186 | B2 | 7/2006 | Robichaud et al. |
| 7,071,201 | B2 | 7/2006 | Kitazawa et al. |
| 7,081,455 | B2 | 7/2006 | Robichaud et al. |
| 7,109,339 | B2 | 9/2006 | Lee et al. |
| 7,115,784 | B2 | 10/2006 | Buchwald et al. |
| 7,118,763 | B2 | 10/2006 | Mesens et al. |
| 7,183,282 | B2 | 2/2007 | Robichaud et al. |
| 7,223,870 | B2 | 5/2007 | Ghosh et al. |
| 7,223,879 | B2 | 5/2007 | Buchwald et al. |
| RE39,679 | E | 6/2007 | Robichaud et al. |
| RE39,680 | E | 6/2007 | Robichaud et al. |
| 7,238,690 | B2 | 7/2007 | Robichaud et al. |
| 7,238,960 | B2 | 7/2007 | Sundaram et al. |
| 7,244,734 | B2 | 7/2007 | Bakker et al. |
| 7,247,731 | B2 | 7/2007 | Buchwald et al. |
| 7,307,091 | B2 | 12/2007 | Alken et al. |
| 7,323,608 | B2 | 1/2008 | Buchwald et al. |
| 7,375,226 | B2 | 5/2008 | Jolidon et al. |
| 7,462,641 | B2 | 12/2008 | Igo et al. |
| 7,517,990 | B2 | 4/2009 | Ito et al. |
| 7,547,452 | B2 | 6/2009 | Mesens et al. |
| 7,592,454 | B2 | 9/2009 | Lee et al. |
| 7,598,273 | B2 | 10/2009 | Gant et al. |
| 7,601,740 | B2 | 10/2009 | Weiner et al. |
| 7,614,727 | B2 | 11/2009 | Hori |
| 7,645,752 | B2 | 1/2010 | McDevitt et al. |
| 7,659,285 | B2 | 2/2010 | Weiner et al. |
| 7,713,995 | B2 | 5/2010 | Weiner et al. |
| 7,732,462 | B2 | 6/2010 | Weiner et al. |
| 7,750,168 | B2 | 7/2010 | Potyen et al. |
| 7,968,538 | B2 | 6/2011 | Becker et al. |
| 7,994,193 | B2 | 8/2011 | Weiner et al. |
| 7,998,971 | B2 | 8/2011 | Barlow et al. |
| 8,008,323 | B2 | 8/2011 | Weiner et al. |
| 8,227,487 | B2 | 7/2012 | Weiner et al. |
| 8,309,722 | B2 | 11/2012 | Tomesch et al. |
| 8,377,959 | B2 | 2/2013 | Weiner et al. |
| 8,414,922 | B2 | 4/2013 | Bryson et al. |
| 8,461,148 | B2 | 6/2013 | Hollander |
| 8,475,793 | B2 | 7/2013 | De Waal Malefyt et al. |
| 8,598,119 | B2 | 12/2013 | Mates et al. |
| 8,603,514 | B2 | 12/2013 | Yang et al. |
| 8,604,021 | B2 | 12/2013 | Becker et al. |
| 8,618,130 | B2 | 12/2013 | Weiner et al. |
| 8,633,180 | B2 | 1/2014 | Li et al. |
| 8,648,077 | B2 | 2/2014 | Tomesch et al. |
| 8,652,378 | B1 | 2/2014 | Yang et al. |
| 8,697,700 | B2 | 4/2014 | Surman et al. |
| 8,778,893 | B2 | 7/2014 | Gong et al. |
| 8,779,139 | B2 | 7/2014 | Tomesch et al. |
| 8,791,138 | B2 | 7/2014 | Seeman et al. |
| 8,835,459 | B2 | 9/2014 | Kottayil et al. |
| 8,900,497 | B2 | 12/2014 | Yang et al. |
| 8,900,498 | B2 | 12/2014 | Yang et al. |
| 8,906,277 | B2 | 12/2014 | Yang et al. |
| 8,921,393 | B2 | 12/2014 | Weiner et al. |
| 8,993,572 | B2 | 3/2015 | Mates et al. |
| 9,067,955 | B2 | 6/2015 | Buchwald et al. |
| 9,108,340 | B2 | 8/2015 | Yang et al. |
| 9,168,258 | B2 | 10/2015 | Mates et al. |
| 9,199,995 | B2 | 12/2015 | Tomesch et al. |
| 9,211,289 | B2 | 12/2015 | Weiner et al. |
| 9,216,175 | B2 | 12/2015 | Amancha et al. |
| 9,315,504 | B2 | 4/2016 | Tomesch et al. |
| 9,371,324 | B2 | 6/2016 | Mates et al. |
| 9,393,192 | B2 | 7/2016 | Yam et al. |
| 9,427,412 | B2 | 8/2016 | Bryson et al. |
| 9,428,506 | B2 | 8/2016 | Mates et al. |
| 9,566,271 | B2 | 2/2017 | Weiner et al. |
| 9,567,327 | B2 | 2/2017 | Xiong et al. |
| 9,586,960 | B2 | 3/2017 | Tomesch et al. |
| 9,616,061 | B2 | 4/2017 | Mates et al. |
| 9,708,322 | B2 | 7/2017 | Li et al. |
| 9,745,300 | B2 | 8/2017 | Mates et al. |
| 9,751,883 | B2 | 9/2017 | Tomesch et al. |
| 9,956,227 | B2 | 5/2018 | Vanover et al. |
| 10,028,944 | B2 | 7/2018 | Weiner et al. |
| 10,072,010 | B2 | 9/2018 | Li et al. |
| 10,077,267 | B2 | 9/2018 | Mates et al. |
| 10,117,867 | B2 | 11/2018 | Mates et al. |
| 10,118,926 | B2 | 11/2018 | Koolman et al. |
| 10,179,776 | B2 | 1/2019 | Davis et al. |
| 10,221,176 | B2 | 3/2019 | Tomesch et al. |
| 10,245,260 | B2 | 4/2019 | Yao et al. |
| 10,322,134 | B2 | 6/2019 | Vanover et al. |
| 10,464,938 | B2 | 11/2019 | Tomesch et al. |
| 10,472,359 | B2 | 11/2019 | Li et al. |
| 10,525,046 | B2 | 1/2020 | Weiner et al. |
| 10,533,015 | B1 | 1/2020 | Tusche et al. |
| 10,597,394 | B2 | 3/2020 | Mates et al. |
| 10,597,395 | B2 | 3/2020 | Tomesch et al. |
| 10,654,854 | B2 | 5/2020 | Li et al. |
| 10,688,097 | B2 | 6/2020 | Yao et al. |
| 10,695,345 | B2 | 6/2020 | Li et al. |
| 10,702,522 | B2 | 7/2020 | Mates et al. |
| 10,716,786 | B2 | 7/2020 | Li et al. |
| 10,799,500 | B2 | 10/2020 | Yao et al. |
| 10,844,061 | B2 | 11/2020 | Li et al. |
| 10,899,762 | B2 | 1/2021 | Mates et al. |
| 10,960,009 | B2 | 3/2021 | Vanover et al. |
| 10,960,010 | B2 | 3/2021 | Vanover et al. |
| 11,014,925 | B2 | 5/2021 | Li et al. |
| 11,026,951 | B2 | 6/2021 | Mates et al. |
| 11,052,083 | B2 | 7/2021 | Li et al. |
| 11,052,084 | B2 | 7/2021 | Li et al. |
| 11,053,245 | B2 | 7/2021 | Mates et al. |
| 11,066,407 | B2 | 7/2021 | Tomesch et al. |
| 11,096,944 | B2 | 8/2021 | Yao et al. |
| 11,124,514 | B2 | 9/2021 | Mates et al. |
| RE48,825 | E | 11/2021 | Tomesch et al. |
| RE48,839 | E | 12/2021 | Mates et al. |
| 11,292,793 | B2 | 4/2022 | Peddy et al. |
| 11,311,536 | B2 | 4/2022 | Li et al. |
| 11,331,316 | B2 | 5/2022 | Li et al. |

(56) References Cited

U.S. PATENT DOCUMENTS

| | | | |
|---|---|---|---|
| 11,332,469 | B2 | 5/2022 | Mittelman et al. |
| 11,407,751 | B2 | 8/2022 | Tomesch et al. |
| 11,440,911 | B2 | 9/2022 | Wennogle et al. |
| 11,453,670 | B2 | 9/2022 | Li et al. |
| 11,560,382 | B2 | 1/2023 | Mates et al. |
| 11,680,065 | B2 | 6/2023 | Li et al. |
| 11,690,842 | B2 | 7/2023 | Li et al. |
| 11,723,909 | B2 | 8/2023 | Yao et al. |
| 11,806,347 | B2 | 11/2023 | Li et al. |
| 11,806,348 | B2 | 11/2023 | Li et al. |
| 11,844,757 | B2 | 12/2023 | Yao et al. |
| 11,957,791 | B2 | 4/2024 | Li et al. |
| 11,958,852 | B2 | 4/2024 | Mates et al. |
| 11,980,617 | B2 | 5/2024 | Snyder et al. |
| 12,070,459 | B2 | 8/2024 | Li et al. |
| 12,090,155 | B2 | 9/2024 | Mates et al. |
| 12,122,792 | B2 | 10/2024 | Li et al. |
| 12,128,043 | B2 | 10/2024 | Li et al. |
| 12,144,808 | B2 | 11/2024 | Li et al. |
| 12,240,850 | B2 | 3/2025 | Li et al. |
| 12,264,160 | B2 | 4/2025 | Li et al. |
| 12,268,686 | B2 | 4/2025 | Li et al. |
| 2001/0008942 | A1 | 7/2001 | Buchwald et al. |
| 2004/0034015 | A1 | 2/2004 | Robichaud et al. |
| 2004/0092534 | A1 | 5/2004 | Yam et al. |
| 2004/0127482 | A1 | 7/2004 | Robichaud et al. |
| 2004/0142970 | A1 | 7/2004 | Chung et al. |
| 2004/0186136 | A1 | 9/2004 | Alken et al. |
| 2005/0166771 | A1 | 8/2005 | Gygi et al. |
| 2005/0182749 | A1 | 8/2005 | Matsui |
| 2005/0222209 | A1 | 10/2005 | Zeldis et al. |
| 2005/0222238 | A1 | 10/2005 | Alken |
| 2006/0178362 | A1 | 8/2006 | Robichaud et al. |
| 2006/0205787 | A1 | 9/2006 | Muller et al. |
| 2008/0069885 | A1 | 3/2008 | Mesens et al. |
| 2008/0132552 | A1 | 6/2008 | Kleinman et al. |
| 2008/0194582 | A1 | 8/2008 | Mates et al. |
| 2008/0280941 | A1 | 11/2008 | Lourtie |
| 2009/0076159 | A1 | 3/2009 | Czarnik |
| 2009/0209608 | A1 | 8/2009 | Czarnik |
| 2010/0159033 | A1 | 6/2010 | Gant et al. |
| 2011/0033542 | A1 | 2/2011 | Myers et al. |
| 2011/0269777 | A1 | 11/2011 | Furuya |
| 2014/0080816 | A1 | 3/2014 | Koolman et al. |
| 2015/0038519 | A1 | 2/2015 | Mates et al. |
| 2015/0072964 | A1 | 3/2015 | Mates et al. |
| 2015/0374684 | A1 | 12/2015 | Javitt et al. |
| 2016/0354315 | A1 | 12/2016 | Li |
| 2017/0114037 | A1 | 4/2017 | Davis et al. |
| 2019/0071445 | A1 | 3/2019 | Li et al. |
| 2019/0211015 | A1 | 7/2019 | Mittelman et al. |
| 2019/0231780 | A1 | 8/2019 | Yao et al. |
| 2019/0328692 | A1 | 10/2019 | Doller et al. |
| 2019/0328745 | A1 | 10/2019 | Vanover et al. |
| 2020/0148683 | A1 | 5/2020 | Peddy et al. |
| 2020/0392135 | A1 | 12/2020 | Wennogle et al. |
| 2021/0009592 | A1 | 1/2021 | Li et al. |
| 2021/0186962 | A1 | 6/2021 | Davis et al. |
| 2021/0220280 | A1 | 7/2021 | Li et al. |
| 2022/0024924 | A1 | 1/2022 | Janton et al. |
| 2022/0048910 | A1 | 2/2022 | Li et al. |
| 2022/0160704 | A2 | 5/2022 | Torralva |
| 2023/0312573 | A1 | 10/2023 | Li et al. |
| 2023/0372336 | A1 | 11/2023 | Dutheil et al. |
| 2024/0122924 | A1 | 4/2024 | Dutheil et al. |
| 2025/0101029 | A1 | 3/2025 | Li et al. |
| 2025/0195510 | A1 | 6/2025 | Dutheil et al. |

FOREIGN PATENT DOCUMENTS

| | | | | |
|---|---|---|---|---|
| WO | WO 1994/024125 | | | 10/1994 |
| WO | WO 1995/026325 | | | 10/1995 |
| WO | WO 1999/043643 | | | 9/1999 |
| WO | WO 2000/002887 | | | 1/2000 |
| WO | WO 2000/048610 | | | 8/2000 |
| WO | WO 2000/064899 | | | 11/2000 |
| WO | WO 2014/110322 | | | 7/2014 |
| WO | WO 2017/117514 | | | 7/2017 |
| WO | WO-2017117514 | A1 | * | 7/2017 |
| WO | WO 2018/106916 | | | 6/2018 |
| WO | 2018/189646 | A1 | | 10/2018 |
| WO | 2019/067591 | A1 | | 4/2019 |
| WO | 2019/236889 | A1 | | 12/2019 |
| WO | 2019/241278 | A1 | | 12/2019 |
| WO | 2020/047241 | A1 | | 3/2020 |
| WO | 2020/112941 | A2 | | 6/2020 |
| WO | 2023/225620 | A1 | | 11/2023 |

OTHER PUBLICATIONS

Angst et al. "Prevalence and Characteristics of Undiagnosed Bipolar Disorders in Patients With a Major Depressive Episode", Arch Gen Psychiatry, vol. 68(8), p. 701-709, (2011).

Avendano, C., et al., "The problem of the existence of C(Ar)—H . . . N Intramolecular Hydrogen Bonds in a Family of 9-Azaphenyl-9H-carbazoles," *J. Chem. Soc. Perkin Trans*., vol. 2, pp. 1547-1555, (1993).

Baille, T.A., "The Use of Stable Isotopes in Pharmacological Research," Pharmacol. Reviews, vol. 33, No. 2, pp. 81-132, (1981).

Balbach, S., et al., "Pharmaceutical evaluation of early development candidates 'the 100 mg-approach'", International Journal of Pharmaceutics, vol. 275, p. 1-12 (2004).

Bastin, R., et al.,"Salt Selection and Optimisation Procedures for Pharmaceutical New Chemical Entities", Organic Process and Research Development, vol. 4, No. 5, pp. 427-435 (2000).

Bechtold, D.A., et al., "Circadian Dysfunction in Disease," *Trends in Pharmacological Sciences*,vol. 31, No. 5, pp. 191-198, (2010); DOI: 10.1016/j.tips.2010.01.002.

Beletskaya, I.P., et al., "Pd- and Cu-catalyzed selective arylation of benzotriazole," *Tetrahedron Letters*, vol. 39, pp. 5617-5620, (1998).

Boger, D., et al., "Inverse Electron Demand Diels-Alder Reactions of Heterocyclic Aza Dienes. Studies on the Total Synthesis of Lavendamycin: Investigative Studies on the Preparation of the CDE β-Carboline Ring System and AB Quinoline-5,8-quinone Ring System" J. Org. Chem., vol. 50, p. 5782-5789, (1985).

Bowman, W.R., et al., "Copper (1) Catalysed Aromatic Nucleophilic Substitution: A Mechanistic and Synthetic Comparison with the $S_{RN}$ 1 Reaction", Tetrahedron Letters, vol. 25(50) p. 5821-5824, (1984).

Bowman, W.R., et al., "Intramolecular Aromatic Substitution ($S_{RN}$1) Reactions—Use of Entrainment for the Preparation of Benzothiazoles," *Tetrahedron Letters*, vol. 23, pp. 5093-5096, (1982).

Bowman, W.R., et al.,"Synthesis of 1H-quinazoline-4-ones using intramolecular aromatic nucelophilic substitution," *Arkivoc*, vol. x, pp. 434-442 (2003).

Bremner et al., "Neuroimaging of Posttraumatic Stress Disorder", Psychiatric Annals Journal, vol. 28, Issue 8, p. 445-450, (1998).

Browne, T.R., "Stable Isotope Techniques in Early Drug Development: An Economic Evaluation," J. Clin. Pharmacol., vol. 38, pp. 213-220, (1998).

Bryan-Lluka, L. J. et al., "Potencies of haloperidol metabolites as inhibitors of the human noradrenaline, dopamine and serotonin transporters in transfected COS-7 cells", *Naunyn-Shemiedeberg's Arch Pharmacol*, 1999, vol. 360, pp. 109-115.

Byrn, S., et al., "Pharmaceutical Solids: A Strategic Approach to Regulatory Considerations", Pharmaceutical Research, vol. 12, No. 7, p. 945-954 (1995).

Caira, et al., "Crystalline Polymorphism of Organic Compounds," Topics in Current Chemistry, vol. 198, p. 163-203, (1998).

Cherrah, Y., et al., "Study of Deuterium Isotope Effects on Protein Binding by Gas Chromatography/Mass Spectrometry. Caffeine and Deuterated Isotopomers," Biomedical and Environmental Mass Spectrometry, vol. 14, pp. 653-657, (1987).

Crawford, K., et al., "Copper-Catalyzed amidations of bromo substituted furans and thiophenes", Tetrahedron Letters, vol. 43, p. 7365-7368, (2002).

Darmani, N. A., et al., "Do Functional Relationships Exist Between 5-$HT_{1A}$ and 5-$HT_2$ Receptors?," *Pharmacology and Biochemistry & Behavior*, vol. 36, p. 901-906, (1990).

(56) References Cited

OTHER PUBLICATIONS

Davis et al., "ITI-007 in the treatment of schizophrenia: from novel pharmacology to clinical outcomes," Expert Review of Neurotherapeutics, vol. 16, No. 6, pp. 601-614 (2016).
Davis et al., "ITI-007: A Novel Treatment for Behavioral Disturbances Associated with Dementia and Related Disorders," Clinical Trials in Alzheimer's Disease (CTAD) Congress 2014 (2014) (poster presentation).
Davis et al., "Rationale for the Development of Low Doses of ITI-007 for the Treatment of Behavioral Disturbances Associated with Dementia," The Journal of Prevention of Alzheimer's Disease, 2(4):302 (2015) (Clinical Trials in Alzheimer's Disease (CTAD) Congress, Symposium Summary OC51).
Davis, et al., "ITI-007 demonstrates brain occupancy at serotonin 5-HT2A and dopamine D2 receptors and serotonin transporters using positron emission tomography in healthy volunteers," *Psychopharmacology*, vol. 232, pp. 2863-2872, (2015); DOI: 10.1007/s00213-015-3922-1.
Davis, et al., "Lumateperone (ITI-007), A Novel Drug in Development for the Treatment of Agitation in Patients with Dementia, including Alzheimer's Disease: Rationale and Clinical Design," The Journal of Prevention of Alzheimer's Disease, 4(4):372 (2017) (Clinical Trials in Alzheimer's Disease (CTAD) Congress, Symposium Summary p. 93.
Dyck, L.E., et al., "Effects of Deuterium Substitution on the Catabolismof β-Phenylethylamine: An In Vivo Study," Journal of Neurochemistry, vol. 46, Issue 2, pp. 399-404, (1986).
Ellenbroek et al., "Animal Models for the Negative Symptoms of Schizophrenia," *Behavioural Pharmacology*, vol. 11, pp. 223-233, (2000).
Evindar, G., et al., "Copper- and Palladium-Catalyzed Intramolecular Aryl Guanidinylation: An Efficient Method for the Synthesis of 2-Aminobenzimidazoles", *Organic Letters*, vol. 5, No. 2, p. 133-136, (2003).
Ezquerra, J., et al., "Efficient Reagents for the Synthesis of 5-, 7-, and 5, 7-Substitued Indoles Starting from Aromatic Amines: Scope and Limitations", J. Org. Chem., vol. 61, p. 5804-5812, (1996).
Fawcett, J., "Posttraumatic Stress Disorder, Stress, and Happiness", Psychiatric Annals Journal, vol. 28, Issue 8, p. 427-428, (1998).
Fee, W.W., et al., "Copper (II)-promoted solvolyses of nickel (II) complexes III. Tetradentate Schiff base ligands containing various diamine segments," *Aust. J. Chem.*, vol. 26, pp. 1475-1485, (1973).
Ferreira, I., et al., "Novel synthetic routes to thienocarbazoles via palladium or copper catalyzed amination or amidation of arylhalides and intramolecular cyclization", *Tetrahedron*, vol. 58, p. 7943-7949, (2002).
Finet, J-P., et al., "Recent advances in ullmann reaction: copper (II) diacetate catalysed N-, )- and S-arylation involving polycoordinate heteroatomic derivatives," *Current Organic Chemistry*, vol. 6, pp. 597-626, (2002).
Fletcher, P., et al., "Perceiving is Believing: A Bayesian Approach to Explaining the Positive Symptoms of Schizophrenia," *Nature Reviews/Neuroscience*, vol. 10, pp. 48-58, (2009).
Foster, A.B., "Deuterium Isotope Effects in the Metabolism of Drugs and Xenobiotics: Implications for Drug Design," 1985, Advances in Drug Research, vol. 14, pp. 1-40.
Foster, P.S., et al., "Acetylcholinesterase inhibitors reduce spreading activation in dementia," *Neuropsychologia*, vol. 50, p. 2093-2099, (2012).
Friedman, M.J.., "Current and Future Drug Treatment for Posttraumatic Stress Disorder Patients", *Psychiatric Annals Journal*, vol. 28, Issue 8, p. 464-468, (1998).
Goodbrand, H.B., et al., "Ligand-Accelerated catalysis of the Ullmann condensation: Application to hole conducting triarylamines," *J. Org. Chem.*, vol. 64, pp. 670-674, (1999).
Gouyette, A., "Synthesis of Deuterium-labelled Elliptinium and its Use in Metabolic Studies," Biomedical and Environmental Mass Spectrometry, vol. 15, pp. 243-247, (1988).
Gramigna, J, "Lumateperone Safe, Effective for Depressive Symptoms Among Patients with Bipolar Disorders," *American Society of Clinical Psychopharmacology Annual Meeting*, Jun. 2, 2020, 3 pages.
Grant, D., "Theory and Origin and Polymorphism", Polymorphism in Pharmaceutical Solids, Chapter 1, p. 1-10 (1999).
Guillory, J.K., "Generation of Polymorphs, Hydrates, Solvates, and Amorphous Solids", Polymorphism in Pharmaceutical Solids, Chapter 5, p. 183-226 (1999).
Hackam, D., et al., "Translation of Research Evidence from Animals to Humans", JAMA, vol. 296, No. 14, p. 1731-1732 (2006).
Hamann, B., et al., "Systematic Variation of Bidentate Ligands used in Aryl Halide Amination. Unexpected Effects of Steric, Electronic, and Geometric Perturbations", *J. Am. Chem. Soc.*, vol. 120, p. 3694-3703, (1998).
Harbert, C.A. et al., "Neuroleptic Activity in 5-Aryltetrahydro-y-carbolines", *J. Med. Chem.*, vol. 23, pp. 635-643 (1980).
Hartwig, J., "Palladium-catalyzed amination of aryl halides: Mechanism and rational catalyst design," *Synlett*, pp. 329-340, (1996).
Harvey et al., "Lumateperone Improves Negative Symptoms Related to Emotional Experience (Avolition) in Patient with Schizophrenia," Abstract presented at the American Society of Clinical Psychopharmacology (ASCP) Annual Meeting; May 29-Jun. 1, 2018; Miami, FL.
Harvey, B.H., et al., "Serotonin and Stress: Protective or Malevolent Actions in the Biobehavioral Response to Repeated Trauma?" Annals of the New York Academy of Sciences, vol. 1032, p. 267-272; DOI: 10.1196/annals.1314.035 (2004).
Haskins, N.J., "The Application of Stable Isotopes in Biomedical Research," Biological Mass Spectrometry, vol. 9, No. 7, pp. 269-277, (1982).
Hassan, J., et al., "Aryl-aryl bond formation one century after the discovery of the ullmann reaction," *Chem. Rev.*, vol. 102, pp. 1359-1469, (2002).
Haynes, et al., "Occurrence of Pharmaceutically Acceptable Anions and Cations in the Cambridge Structural Database", *Journal of Pharmaceutical Sciences*, vol. 94, No. 10, p. 2111-2120 (2005).
Hlavinka, E., "Schizophrenia Tx Eases Depression in Bipolar Disorder: Lumateperone Offers Greater Rate of Response, Remission versus Placebo," *Medpage Today*, 7 pages, (2020); https://www.medpagetoday.com/meetingcoverage/psychcongress/88584.
Honma, S., et al., "The Metabolism of Roxatidine Acetate Hydrochloride: Liberation of Deuterium from the Piperidine Ring during Hydroxylation," Drug Metabolism and Disposition, vol. 15, No. 4, pp. 551, (1987).
Howland, R.H., "Deuterated Drugs," Journal of Psychosocial Nursing and Mental Health Services, 53(9): 13-16 (2015).
International Search Report issued in the International Application No. PCT/US2019/023687, mailed Jun. 10, 2019, 3 pages.
Ito, T., et al., "Studies of organic catalytic reactions. VI. The function of pyridine and copper in the Rosenmund-von Braun reaction," *Bulletin of the Chemical Society of Japan* vol. 41, pp. 419-423, (1968).
Izrayelit, L., "Schizoaffective Disorder and PTSD Successfully Treated With Olanzapine and Supportive Psychotherapy", Psychiatric Annals Journal, vol. 28, Issue 8, p. 424-426, (1998).
Jain et al., "Polymorphism in Pharmacy," Indian Drugs, vol. 23, No. 6, pp. 315-316 (1986).
Ji, J., et al., "Selective amination of polyhalopyridines catalyzed by a palladium-xantphos complex," *Organic Letters*, vol. 5, No. 24, pp. 4611-4614, (2003).
Jordan, V.C., "Tamoxifen: A Most Unlikely Pioneering Medicine", Nature Reviews: Drug Discovery, vol. 2, p. 205-213, (2003).
Juorio, A. V., et al., "Effects of Acute and Chronic Phenelzine on Regional Monoamine Metabolism in Rats and its Potentiation by Deuterium Substitution," Naunyn-Schmiedeberg's Archives of Pharmacology, vol. 333, No. 3, pp. 240-245, (1986); Abstract only.
Kahn, A., et al., "Residual Symptoms of Schiziphrenia. What are Realistic Treatment Goals? Lingering Symptoms Require you to Evaluate Pharmacotherapy and Offer Psychosocial Interventions," *Current Psychiatry*, vol. 16, No. 3, pp. 35-40, (2017).
Kametani, T., et al., "A Novel Synthesis of Indole Derivatives", *Heterocycles*, vol. 14, No. 3, p. 277-280, (1980).

(56) References Cited

OTHER PUBLICATIONS

Kang, S-K., et al., "Copper-catalyzed N-arylation of aryl iodides with benzamides or nitrogen heterocycles in the presence of ethylendiamine," *Synlett*, No. 3, pp. 427-430, (2002).
Kay, S.R., et al., "The Positive and Negative Syndrome Scale (PANSS) for Schizophrenia," *Schizophrenia Bulletin*, vol. 13, Issue 2, pp. 261-276, (1987).
Kessler, R.C., et al., "Lifetime Prevalence and Age-of-Onset Distributions of DSM-IV Disorders in the National Comorbidity Survey Replication", Arch Gen Psychiatry; vol. 62, p. 593-602, (2005).
Khorana, N., et al., "Gamma-Carbolines: Binding at 5-HT5A Serotonin Receptors", *Bioorganic & Medicinal Chemistry*, vol. 11, pp. 717-722, p. 718 Table 1, (2003).
Kiyomori, A., et al., "An efficient copper-catalyzed coupling of aryl halides with imidazoles," *Tetrahedron Letters*, vol. 40, pp. 2657-2660, (1999).
Klapars, A., et al., "A general and efficient copper catalyst for the amidation of aryl halides and the N-arylation of nitrogen heterocycles," *J. Am. Chem. Soc*., vol. 123, pp. 7727-7729, (2001).
Klapars, A., et al., "A general and efficient copper catalyst for the amidation of aryl halides," *J. Am. Chem. Soc*., vol. 124, pp. 7421-7428, (2002).
Kondratov, S.A., et al., "Nucelophilic substitution in the aromatic series. Lv. Reaction of o-nitrochlorobenzene with ammonia in the presence of copper compounds," *Zhurnal Organidreskoi Khimii*, vol. 51, No. 11, pp. 2387-2390, (1979).
Koppel, J., et al., "Optimal Treatment of Alzheimer's Disease Psychosis: Challenges and Solutions," *Neuropsychiatric Disease and Treatment*, vol. 10, pp. 2253-2262, (2014).
Krystal, J.H., et al., "Adjunctive Risperidone Treatment for Antidepressant-Resistant Symptoms of Chronic Military Service-Related PTSD: A Randomized Trial," *JAMA*, vol. 306, No. 5, pp. 493-502, (2011).
Kwong, F.Y., et al., "Mild and efficient copper-catalyzed amination of aryl bromides with primary alkylamines," *Organic Letters*, vol. 5, No. 6, pp. 793-796, (2003).
Lammers, et al., "Risperidone Long-acting Injection in Schizophrenia Spectrum Illnesses Compared to First Generation Depot Antipsychotics in an Outpatient Setting in Canada," BMC Psychiatry, vol. 13, No. 155, 9 pages, (2013); http://www.biomedcentral.com/1471-244X/13/155.
Laughren, et al., "Food and Drug Administration Commentary on Methodological Issues in Negative Symptom Trials," Schizophrenia Bulletin, 37(2): 255-256 (2011).
Lebert, F., et al., "Trazodone in Fronto-Temporal Dementia", *Research and Practice in Alzheimer's Disease*, vol. 11, 356-360, (2006).
Lee, T., et al. "Novel, Highly Potent, Selective 5-$HT_{2A}/D_2$ Receptor Antagonists as Potential Atypical Antipsychotics," *Bioorg. Med. Chem. Lett*. vol. 13, pp. 767-770, (2003).
Li et al., "Discovery of a Tetracyclic Quinoxaline Derivative as a Potent and Orally Active Multifunctional Drug Candidate for the Treatment of Neuropsychiatric and Neurological Disorders", Journal of Medicinal Chemistry, vol. 57, p. 2670-2682 (2014).
Lieberman, J.A., et al., "ITI-007 for the Treatment of Schizophrenia: A 4-Week Randomized, Double-Blind, Controlled Trial," *Biol. Psychiatry*, vol. 79, No. 12, pp. 952-961, (2015).
Lin, Y-T., et al., "Dosage and Duration of Antipsychotic Treatment in Demented Outpatients with Agitation or Psychosis," *Journal of the Formosan Medical Association*, vol. 114, pp. 147-153, (2015).
Lipschitz, D.S., et al., "Childhood Posttraumatic Stress Disorder: A Review of Neurobiologic Sequelae", Psychiatric Annals Journal, vol. 28, Issue 8, p. 452-457, (1998).
Lopez, et al., "Psychiatric Symptoms Vary with the Severity of Dementia in Probably Alzheimer's Disease," *J. Neuropsychiatry Clin. Neurosc*., vol. 15, No. 3, pp. 346-353, (2003).
Louie, J., et al., "Palladium-Catalyzed Synthesis of Arylamines from Aryl Halides, Mechanistic Studies lead to Coupling in the Absence of Tin Reagents", *Tetrahedron Letters*, vol. 36, No. 21, p. 3609-3612, (1995).
Lounkine, E., et al.,"Formal Concept Analysis for the Identification of Molecular Fragment Combinations Specific for Active and Highly Potent Compounds," *J. Med. Chem*., vol. 51, No. 17, pp. 5342-5348, (2008).
Madhusoodanan, S., et al., "Pharmacological Management of Behavioral Symptoms Associated with Dementia," *World J. Psychiatr*., vol. 4, No. 4, pp. 72-79, (2014).
Makadia et al., "Poly Lactic-co-Glycolic Acid (PLGA) as Biodegradable Controlled Drug Delivery Carrier," *Polymers* (*Basel*), vol. 3, No. 3, pp. 1377-1397, (2011).
Marcoux, J-F., et al., "A general copper-catalyzed synthesis of diaryl ethers," *J. Am. Chem. Soc*., vol. 119, pp. 10539-10540, (1997).
Marek et al. Synergistic Action of 5-HT2A Antagonists and Selective Serotonin Reuptake Inhibitors in Neuropsychiatric Disorders. Neuropsychopharmacology, 2003. vol. 28, pp. 402-412. (Year: 2003).
Medisorb Fact Sheet in Medisorb Microspheres Technology (Jan. 2009) at https://static.secure.website/wscfus/6472891/uploads/Medisorb.pdf (retrieved from the internet May 18, 2020) (Year: 2009).
Mohamed, S., et al., "Pharmacotherapy of PTSD in the U.S. Department of Veterans Affairs: diagnostic- and symptom-guided drug selection", *J. Clin. Psychiatry*, vol. 69, pp. 959-965, (2008).
Morgan, C.A., et al., "Acoustic Startle in Individuals With Posttraumatic Stress Disorder", Psychiatric Annals Journal, vol. 28, Issue 8, p. 430-434, (1998).
Mueller, et al., "Detection of Depression in Acute Schizophrenia: Sensitivity and Specificity of 2 Standard Observer Rating Scales," *Can J Psychiatry*, vol. 51, No. 6, pp. 387-392, (2006).
Mulrooney, C., et al., "Recent developments in copper-catalyzed n-arylation with aryl halides," Essay—University of Pennsylvania (2004).
Murakami et al., "Fischer Indolization of Ethyl Pyruvate 2-[2-(Trifluoromethyl) phenyl]-phenylhydrazone and New Insight into the Mechanism of the Goldberg Reaction." *Chem. Pharm. Bull*., vol. 43, No. 8, p. 1281-1286, (1995).
Nagai, Y., et al., "Synthesis of 2,3,4,4a,5,9b-hexahydro-1H-pyrido[4,3-b] indole derivatives and their central nervous system activities." *Journal of Medicinal Chemistry*, vol. 22, No. 6, p. 677-683, (1979).
Newman, A.W., et al., "Solid-state analysis of the active pharmaceutical ingredient in drug products", *Drug Discovery Today*, vol. 8, No. 19, 898-903 (2003).
Nihon rounen igaku zasshi, vol. 48, No. 3, pp. 195-204, (2011 nen). English translation only, 2 pages.
Noble, F., et al., "The Opioid Receptors as Targets for Drug Abuse Medication," *British Journal of Pharmacology*, vol. 172, pp. 3964-3979, (2015); DOI: 10.1111/bph.13190.
O'Gorman, et al., "Lumateperone (ITI-007): A Novel Investigational Agent with Broad Therapeutic Potential Across Multiple Neuropsychiatric Disorders," Poster p. 1.g.038, European College of Neuropsychopharmacology (ECNP) Congress (2017).
Perlis et al., "Clinical Features of Bipolar Depression Versus Major Depressive Disorder in Large Multicenter Trials", Am J Psychiatry, vol. 163, p. 225-231, (2006).
Pieniaszek, H.J., et al., "Moricizine Bioavailability via Simultaneous Dual, Stable Isotope Administration: Bioequivalence Implications," J. Clin. Pharmacol., vol. 39, pp. 817-825, (1999).
Pine, A., et al., "Dopamine, Time, and Impulsivity in Humans," *The Journal of Neuroscience*, vol. 30, No. 26, pp. 8888-8896.
Press Release, "Intra-Cellular Therapies Announces Additional Results from Phase I/II Clinical Trail for ITI-007 in Healthy Geriatric Subjects and Patients With Dementia," Intra-Cellular Therapies, Press Release Date: Nov. 21, 2014, (http://ir.intracellulartherapies.com/releasedetail.cfm?ReleaseID=884325), accessed on May 31, 2016.
Press Release, "Intra-Cellular Therapies Announces Positive Top-Line Results from a Phase 3 Trial of Lumateperone in Patient with Bipolar Depression," Intra-Cellular Therapies, Press Release Date: Jul. 8, 2019, (https://ir.intracellulartherapies.com/news-releases/news-release-details/intra-cellular-therapies-announces-positive-top-line-results-0), accessed on Aug. 29, 2019.
PubChem, Open Chemistry Database, Compound Summary for CID-22036753, pp. 4, (2007), 12 pages.

(56) References Cited

OTHER PUBLICATIONS

PubChem, Open Chemistry Database, PubChem SID 103920954, PubChem CID 90655118, (2011), 6 pages.

Rackova, L., et al., "Free Radical Scavenging and Antioxidant Activities of Substituted Hexahydropyridoindoles. Quantitative Structure-Activity Relationships." *Journal of Medicinal Chemistry*, vol. 49, No. 8, p. 2543-2548, (2006).

Rainer, M.K., "Risperidone long-acting injection: a review of its long term safety and efficacy," *Neuropsychiatric Disease and Treatment*, vol. 4, No. 5, pp. 919-927 (2008).

Reynolds, C.A., et al., "Longitudinal Change in Memory Performance Associated with HTR2A Polymorphism," *Neurobiology of Aging*, vol. 27, pp. 150-154, (2006).

Rye (Sleep Disorders and Parkinson's Disease, 2000, accessed online http://www.waparkinsons.org/edu_research/articles/Sleep_Disorders.html), 2 pages.

Sadighi, J.P., et al., "A highly active palladium catalyst system for the arylation of anilines," *Tetrahedron Letters*, vol. 39, pp. 5327-5330, (1998).

Satlin, et al., "ITI-007 (Lumateperone) for the Treatment of Agitation in Patients with Dementia, including Alzheimer's Disease," Alzheimer's & Dementia 14(7) (Suppl.): p. 678-79 (2018) (Alzheimer's Assoc. International Conference 2018, summary of Poster P2-032).

Satlin, et al., "ITI-007 (Lumateperone) for the Treatment of Agitation in Patients with Dementia, including Alzheimer's Disease," Poster P2-032, Alzheimer's Assoc. International Conference 2018 (2018).

Savjani, K., et al., "Drug Solubility: Importance and Enhancement Techniques", International Scholarly Research Network Pharmaceutics, vol. 2012, pp. 1-10, (2012).

Schennach, et al., "What Are Residual Symptoms in Schizophrenia Spectrum Disorder? Clinical Description and 1-year Persistence Within a Naturalistic Trial," *Eur. Arch. Psychiatry Clin. Neurosci.*, vol. 265, pp. 107-116, (2015); DOI: 10.1007/s00406-014-0528-2.

Seishinkei Shi, vol. 110, No. 7, pp. 557-584, (2008). Partial English translation only.

Sigel, H., et al., "Tenary Complexes in Solution", *Inorganic Chemistry*, vol. 13, No. 2, p. 462-465 (1974).

Singhal, D., et al., "Drug polymorphism and dosage form design: a practical perspective," *Advanced Drug Delivery Reviews*, vol. 56, pp. 335-347 (2004).

Snyder, G.L., et al., "Functional profile of a novel modulator of serotonin, dopamine, and glutamate neurotransmission," *Psychopharmacology*, vol. 232, p. 605-621 (2015) Published online Aug. 2014, DOI 10.1007/s00213-014-3704-1.

Southwick, S.M., et al., "Neuroendocrine Alterations in Posttraumatic Stress Disorder," Psychiatric Annals Journal, vol. 28, Issue 8, p. 436-442, (1998).

Sugahara, M., et al., "A Facile Copper-Catalyzed Ullman Condensation:N-Arylation of Heterocyclic Compounds Containing an -NHCO- Moiety", *Chem. Pharm. Bull.*, vol. 45, No. 4, p. 719-721, (1997).

Taragano, F.E., et al., "A Double-Blind, Randomized, Fixed-Dose Trial of Fluoxetine vs. Amitriptyline in the Treatment of Major Depression Complicating Alzheimer's Disease," Psychosomatics, vol. 38, Issue 3, p. 246-252, (1997).

Tariot, et al., "Memantine Treatment in Patients with Moderate to Severe Alzheimer Disease Already Receiving Donepezil: A Randomized Controlled Trail," JAMA, vol. 291, No. 3, pp. 317-324, (2004).

Timmins, G.S., "Deuterated drugs: where are we now?" Expert Opinion on Therapeutic Patents, 1-9 (2014).

Tohen, M., et al., "Efficacy of Olanzapine and Olanzapine-Fluoxetine Combination in the Treatment of Bipolar I Depression," *Arch Gen Psychiatry*, vol. 60, pp. 1079-1088, (2003).

Tonn, G.R., et al., "Simultaneous Analysis of Diphenhydramine and a Stable Isotope Analog (2H10)Diphenhydramine Using Capillary Gas Chromatography with Mass Selective Detection in Biological Fluids from Chronically Instrumented Pregnant Ewes," Biological Mass Spectrometry, vol. 22, pp. 633-642, (1993).

Tung, R., "The Development of Deuterium-Containing Drugs," 2010, Innovations in Pharmaceutical Technology, vol. 32, pp. 1-4.

Vanover, et al., "A Novel Approach to Address an Unmet Need in the Treatment of Schizophrenia and Depression: Lumateperone, an Innovative Modulator of Dopamine, Serotonin, and Glutamate," Abstract presented at the American Society of Clinical Psychopharmacology (ASCP) Annual Meeting; May 29-Jun. 1, 2018; Miami, FL.

Vanover, et al., "Dopamine D2 receptor occupancy of lumateperone (ITI-007): a Positron Emission Tomography Study in patients with schizophrenia," Neuropsychopharmacology 44:598-605, (2019).

Vanover, K., et al., "ITI-007: A Novel Therapy for the Treatment of Schizophrenia and Related Psychoses," *International Clinical Psychopharamcology*, vol. 26, e56, 1 page, (2011).

Vloeberghs, E., et al., "Altered Circadian Locomotor Activity in APP23 Mice: A Model for BPSD Disturbances," *European Journal of Neuroscience*, vol. 20, pp. 2757-2766, (2004); DOI: 10.1111/j.1460-9568.2004.03755.x.

Vyas, P., et al., "An Evaluation of Lumateperone Tosylate for the Treatment of Schizophrenia," *Expert Opinion on Pharmacotherapy*, vol. 21, No. 2, pp. 139-145, (2020); https://doi.org/10.1080/14656566.2019.1695778.

Wagaw, S., et al., "A palladium-catalyzed method for the preparation of indoles via the Fischer indole synthesis," *Journal of the American Chemical Society*, vol. 121, No. 44, pp. 10251-10263, (1999).

Wennogle, et al., "Activation of NMDA and AMPA Receptors by Lumateperone (ITI-007): Implications for Antidepressant Activity," Abstract presented at the 2017 Collegium Internationale Neuro-Psychopharmacologicum (CINP) Thematic Meeting: Treatment Resistant Depression; Jul. 20-22, 2017; Prague.

Weschules, D., et al., "Acetylcholinesterase Inhibitor and N-Methyl-D-Aspartic Acid Receptor Antagonist Use among Hospice Enrollees with a Primary Diagnosis of Dementia", *Journal of Palliative Medicine*, vol. 11, No. 5, pp. 738-745 (2008).

Wiese, M., "DSC Detection of Polymorphism in Pharmaceutical Anhydrous Dexamethasone Acetate," *TA Instruments*, TA 302, pp. 1-4 (2002).

Wolen, R. L., "The Application of Stable Isotopes to Studies of Drug Bioavailability and Bioequivalence," J. Clin. Pharmacol., vol. 26, pp. 419-424, (1986).

Wolfe, J.P., et al., "An improved catalyst system for aromatic carbon-nitrogen bond formation: The possible involvement of bis(phosphine) palladium complexes as key intermediates," *J. Am. Chem. Soc.*, vol. 118, pp. 7215-7216, (1996).

Wolfe, J.P., et al., "Intramolecular palladium-catalyzed aryl amination and aryl amidation," *Tetrahedron*, vol. 52, No. 21, pp. 7525-7546, (1996).

Wolter, M., et al., "Synthesis of N-aryl hydrazides by copper-catalyzed coupling of hydrazides with aryl iodides," *Organic Letters*, vol. 3, No. 23, pp. 3803-3805, (2001).

Written Opinion of the International Searching Authority for International Application No. PCT/US2019/023687 mailed Jun. 10, 2019, 5 pages.

Yamada, K., et al., "A mild copper-mediated intramolecular amination of aryl halides," *Synlett*, No. 2, pp. 231-234, (2002).

Yang, B.H., "The development of efficient protocols for the palladium-catalyzed cyclization reactions of secondary amides and carbamates," *Organic Letters*, vol. 1, No. 1, pp. 35-37, (1999).

Yudofsky, S., et al., "Propranolol in the Treatment of Rage and Violent Behavior in Patients with Chronic Brain Syndromes", Am. J. Psychiatry, vol. 138, p. 218-220, (1981).

Zhang, G., et al., "The Role of Serotonin 5-HT2A Receptors in Memory and Cognition," *Front. Pharmacol.*, vol. 6, No. 225, pp. 1-17, (2015); DOI: 10.3389/fphar.2015.00225.

Zhang, Z., et al., "Highly efficient copper-catalyzed N-arylation of alkylamines with aryl iodides using phosphoramidite as ligand", Catalysis Communications, vol. 6, p. 784-787, (2005).

Baba et al., "Studies on drug metabolism by use of isotopes. 23. Metabolic study of 1-butyryl-4-cinnamylpiperazine in the rat during

(56) References Cited

OTHER PUBLICATIONS development of tolerance by using two kinds of deuterium-labeled forms", J. Med. Chem., 21(6), pp. 525-529, (1978).
Timmins, G.S., "Deuterated drugs: where are we now?", *Expert Opin. Ther. Pat.*, 24(10), pp. 1067-1075, (2014).
Cargnin et al., "A Primer of Deuterium in Drug Design," Future Medicinal Chemistry, 11(16):2039-2042 (2019).
Correll et al., "Efficacy and Safety of Lumateperone for Treatment of Schizophrenia a Randomized Clinical Trial," JAMA Psychiatry, vol. 77, No. 4, p. 349-358 (2020).
Edinoff et al., "Lumateperone for the Treatment of Schizophrenia," Psychopharmacology Bulletin, vol. 50, No. 4, p. 32-59 (2020).
Harbeson et al., "Deuterium Medicinal Chemistry: A New Approach to Drug Discovery and Development," Medchem News, 2:8-22 (2014).
Russak et al., "Impact of Deuterium Substitution on the Pharmacokinetics of Pharmaceuticals," Annals of Pharmacotherapy, 1-6 (2018).
Vanover et al., Abstracts of the 13th International Congress on Schizophrenia (ICOSR) (Apr. 2-6, 2011), Schizophrenia Bull. 37 Suppl. 1., p. 325 (Mar. 2011).
Bharate, S., "Recent developments in pharmaceutical salts: FDA approvals from 2015 to 2019," *Drug Discovery Today*, 26(2):384-398 (2021).
Paulekuhn, et al., "Trends in Active Pharmaceutical Ingredient Salt Selection based on Analysis of Orange Book Database," *Journal of Medicinal Chemistry*, 50:6665-6672 (2007).
Alastair J. Florence, "Polymorph screening in pharmaceutical development" European Pharmaceutical Review, Aug. 19, 2010, https://www.europeanpharmaceuticalreview.com/article/3659/polymorphscreening-in pharmaceutical-development/ (retrieved on Mar. 7, 2018).
Bavin, M., "Polymorphism in Process Development," Chemistry & Industry, pp. 527-529, (1989).
Berge, S. et al., "Pharmaceutical Salts," J. Pharm. Sci., vol. 66, No. 1, pp. 1-19, (1977).
Brittain, H. et al., "Chapter 5: Generation of Polymorphs, Hydrates, Solvates, and Amorphous Solids," Polymorphism in Pharmaceutical Solids, 25 pages, (1999).
Calabrese, J. et al., "Efficacy and Safety of Lumateperone for Major Depressive Episodes Associated with Bipolar I or Bipolar II Disorder: A Phase 3 Randomized Placebo-Controlled Trial," American Journal of Psychiatry, vol. 178, No. 12, pp. 1098-1106, (2021), published online Sep. 23, 2021, DOI: https://doi.org/10.1176/appi.aip.2021.20091339.
Dutheil, S., et al. "Lumateperone Normalizes Pathological Levels of Acute Inflammation through Important Pathways Known to Be Involved in Mood Regulation," The Journal of Neuroscience, vol. 43, No. 5, pp. 863-877, (2023).
Fisher et al., "The Complexities Inherent in Attempts to Decrease Drug Clearance by Blocking Sites of CYP-Mediated Metabolism," Current Opinions in Drug Discovery & Development, vol. 9, No. 1, p. 101-109, (2006).
Grant, D., "Polymorphism in Pharmaceutical Solids", Chapter 1, pp. 1-10 (1999).
Jozwiakowski, M., "Alteration of the Solid State of the Drug Substance: Polymorphs, Solvates, and Amorphous Forms," Water-Insoluble Drug Formulation, Interpharm Press, pp. 525, 557-561, (2000).
Liu et al., "Progress in Deuterated Drugs," Chemical Engineering Design Communications, vol. 42, No. 4, p. 199-238; English Abstract Only.
Mcintyre et al., "The Efficacy of Lumateperone in Patients with Bipolar Depression with Mixed Features," J Clin Psychiatry, vol. 84, No. 3, 10 pages (2023).
Mcintyre et al., "The Efficacy of Lumateperone on Symptoms of Depression in Bipolar I and Bipolar II Disorder: Secondary and Post Hoc Analyses," European Neuropsychopharmacology, vol. 68, p. 78-88, (2023).
Mcintyre, R. et al., "Rapid-acting Antidepressants in Psychiatry: Psychedelics, Episodic Treatments, Innovation, and Clarion Call for Methodologic Rigor in Drug Development," Expert Opinion on Drug Safety, vol. 21, No. 6, pp. 715-716, (2022).
Saal, C. et al., "Pharmaceutical Salts: A Summary on Doses of Salt Formers from the Orange Book," European Journal of Pharmaceutical Sciences, vol. 49, pp. 614-623, (2013).
Serajuddin, A., "Salt formation to improve drug solubility," Advanced Drug Delivery Reviews, vol. 59, pp. 603-616, (2007).
Snyder, G. et al., "Chapter 11: A review of the pharmacology and clinical profile of lumateperone for the treatment of schiophrenia," Advances in Pharmacology, vol. 90, pp. 253-276, 31 pages, (2021).
Stahl & Wermouth (Eds.), "Handbook of Pharmaceutical Salts Properties, Selection, and Use," Wiley-VCH, pp. 167-168, 170-173, 216-217 (2002).
Stahl & Wermouth (Eds.), "Handbook of Pharmaceutical Salts Properties, Selection, and Use," Wiley-VCH, pp. 258-261 (2002).
Suppes, T. et al., "Adjunctive lumateperone (ITI-007) in the treatment of bipolar depression: Results from a randomized placebo-controlled clinical trial," Bipolar Disorders, vol. 25, pp. 478-488, 11 pages, (2023).
Vanover, K. et al., "50. ITI-007, an Investigational New Antipsychotic Drug with a Novel Pharmacological Profile, is Safe and Well-Tolerated with Early Clinical Signs for Efficacy in Patients with Stabilized Schizophrenia," Abstract presented at the ANCP 49th Annual Conference in Poster Session III; Dec. 8, 2010; pp. S321-S322; Neuropsychopharmacology, vol. 35, (2010).
Vanover, K. et al., "Safety, Pharmacokinetics and Early Signals for Efficacy with ITI-007, A Novel Investigational New Drug for the Treatment of Schizophrenia and Related Disorders," Schizophrenia Bulletin, vol. 37, Suppl. 1, p. 325, (2011), Abstract only.
Vanover, K. et al., "Lumateperone (ITI-007): A Novel Investigational Agent with Broad Therapeutic Potential Across Multiple Neuropsychiatric Disorders," European Neuropsychopharmacology, vol. 27, pp. S660-S661 (2017) (Summary of ECNP Poster p. 1.g.038).
Vippagunta, S. et al., "Crystalline Solids," Advanced Drug Delivery Reviews, vol. 48, pp. 3-26, (2001).
Wang, S. et al., "Rapid-acting Antidepressants Targeting Modulation of the Glutamatergic System: Clinical and Preclinical Evidence and Mechanisms," General Psychiatry, vol. 35, No. e100922, 6 pages, (2022).
Xu, Y. et al., "Neurotransmitter receptors and cognitive dysfunction in Alzheimer's disease and Parkinson's disease," Progress in Neurobiology, vol. 97, No. 1, pp. 1-13, (2012).
Yiannopoulou, K. et al., "Current and future treatments for Alzheimer's disease," Therapeutic Advances in Neurological Disorders, vol. 6, No. 1, pp. 19-33, (2013).
"Highlights of Prescribing Information Caplyta (lumateperone) capsules, for oral use," Label—Prescribing Information, 16 pages, (2019); https://www.accessdata.fda.gov/drugsatfda_docs/label/2019/209500s000lbl.pdf.
Tilborg, A. et al., "Pharmaceutical Salts and Cocrystals Involving Amino Acids: A Brief Structural Overview of the State-of-Art," European Journal of Medicinal Chemistry, vol. 74, pp. 411-426, (2014).
Ebdrup et al., "Serotonin 2A Receptor Antagonists for Treatment of Schizophrenia," Expert Opin Investig Drugs, vol. 20, No. 9, p. 1211-1223, (2011).
Gibson, Ed., Pharmaceutical Preformulation and Formulation—A Practical Guide from Candidate Drug Selection to Commercial Dosage Form, p. 84 (Informa Healthcare, 2nd Ed., 2009).
Gould, P., "Salt selection for basic drugs," Int'l J. of Pharms., vol. 33, pp. 201-217, 19 pages, (1986).
Hirayama, Noriaki, Handbook of Organic Compound Crystal Preparation, 2008, pp. 17-23, 37-40, 45-51, 57-65.
Intra-Cellular Press Release, "Intra-Cellular Therapies Presents Data on Lumateperone, ITI-214 and ITI-333 at the 56th Annual Meeting of the American College of Neuropsychopharmacology," (Dec. 7, 2017).
Intra-Cellular Press Release, "Intra-Cellular Therapies Reports Initiation of Patient Enrollment for ITI-007 Phase I Clinical Trials in Bipolar Depression", (Dec. 23, 2015).

(56) References Cited

OTHER PUBLICATIONS

ITCI Press Release 2008, "Intra-Cellular Therapies Announces the Discovery of Potent Antidepressant Activity in ITI-007" (Apr. 9, 2008).
Koek et al., "Behavioral Pharmacology of Antagonists at 5-HT2/5-HT1C Receptors," Neuroscience & Biobehavioral Reviews, vol. 16, p. 95-105, (1992).
Rudnic & Schwartz, "Oral Solid Dosage Forms," in Remington: The Science and Practice of Pharmacy, Chap 45, pp. 889-928 (21st Ed., 2005).
Vanover, K. et al., "Pharmacokinetic Profile of ITI-007, A Novel Approach for the Treatment of Schizophrenia and Other Psychiatric and Neurological Disorders" Neuropsychopharmacology, vol. 38 (2012), p. S418 (ACNP 51st Poster Session III: Abstract No. W176).

* cited by examiner

ORGANIC COMPOUNDS

CROSS-REFERENCE TO RELATED APPLICATIONS

This application is a U.S. National Stage application under 35 U.S.C. § 371 of International Application No. PCT/US2019/023687, filed on Mar. 22, 2019, which claims priority to and the benefit of U.S. Provisional Application No. 62/647,482, filed on Mar. 23, 2018, the contents of each of which are hereby incorporated by reference in their entireties.

FIELD OF THE INVENTION

The invention relates to particular deuterated heterocycle fused gamma-carbolines, in free, pharmaceutically acceptable salt and/or substantially pure form as described herein, pharmaceutical compositions thereof, and methods of use in the treatment of diseases involving 5-$HT_{2A}$ receptor, serotonin transporter (SERT) and/or pathways involving dopamine $D_1$/$D_2$ receptor signaling systems, e.g., diseases or disorders such as anxiety, psychosis, schizophrenia, sleep disorders, sexual disorders, migraine, conditions associated with cephalic pain, social phobias, gastrointestinal disorders such as dysfunction of the gastrointestinal tract motility and obesity; depression and mood disorders associated with psychosis or Parkinson's disease; psychosis such as schizophrenia associated with depression; bipolar disorder; and other psychiatric and neurological conditions, as well as to combinations with other agents.

BACKGROUND OF THE INVENTION

Psychosis, particularly schizophrenia and schizoaffective disorder, affects an estimated 1-2% of the population worldwide. Schizophrenia is comprised of three phases: prodromal phase, active phase and residual phase. Prodromal phase is an early phase wherein subclinical signs and symptoms are observed. These symptoms may include loss of interest in usual pursuits, withdrawal from friends and family members, confusion, trouble with concentration, feeling of listlessness and apathy. Active phase is characterized by exacerbations of positive symptoms such as delusions, hallucinations and suspiciousness. Residual phase is characterized by negative symptoms such as emotional withdrawal, passive social withdrawal, and stereotyped thinking; and general psychopathological symptoms including active social avoidance, anxiety, tension, and somatic concerns. Residual phase symptoms also are often accompanied by depression, cognitive dysfunction and insomnia. Collectively, these residual phase symptoms are not well-treated by many antipsychotic drugs currently available on the market and therefore are usually observed after the active phase symptoms have subsided after treatment. This phase of the illness is when patients would like to return to more productive and fulfilling lives, but since the residual negative symptoms and cognitive impairment are not properly treated, it frustrates the return to such a function. There remains an urgent need for anti-psychotic agent, which can treat not just the active or acute phase symptoms, but also the residual phase symptoms of psychosis, e.g., schizophrenia. In addition, there is a need for medications to treat these symptoms that are free from undesirable side effects caused by off-target interactions with histamine H1 and muscarinic acetylcholine receptor systems.

Substituted heterocycle fused gamma-carbolines are known to be agonists or antagonists of 5-HT2 receptors, particularly 5-$HT_{2A}$ receptors, in treating central nervous system disorders. These compounds have been disclosed in U.S. Pat. Nos. 6,548,493; 7,238,690; 6,552,017; 6,713,471; 7,183,282; RE39,680, and RE39,679, as novel compounds useful for the treatment of disorders associated with 5-$HT_{2A}$ receptor modulation such as obesity, anxiety, depression, psychosis, schizophrenia, sleep disorders, sexual disorders migraine, conditions associated with cephalic pain, social phobias, gastrointestinal disorders such as dysfunction of the gastrointestinal tract motility, and obesity.

U.S. Patent Publications 2010/113781 and 2004/209864 disclose methods of making substituted heterocycle fused gamma-carbolines and uses of these gamma-carbolines as serotonin agonists and antagonists useful for the control and prevention of central nervous system disorders such as addictive behavior and sleep disorders.

US 2011/071080 discloses use of particular substituted heterocycle fused gamma-carbolines for the treatment of a combination of psychosis and depressive disorders as well as sleep, depressive and/or mood disorders in patients with psychosis or Parkinson's disease. In addition to disorders associated with psychosis and/or depression, this patent application discloses and claims use of these compounds at a low dose to selectively antagonize 5-$HT_{2A}$ receptors without affecting or minimally affecting dopamine $D_2$ receptors, thereby useful for the treatment of sleep disorders without the side effects of the dopamine $D_2$ pathways or side effects of other pathways (e.g., $GABA_A$ receptors) associated with conventional sedative-hypnotic agents (e.g., benzodiazepines) including but not limited to the development of drug dependency, muscle hypotonia, weakness, headache, blurred vision, vertigo, nausea, vomiting, epigastric distress, diarrhea, joint pains, and chest pains.

Furthermore, it has been discovered that these particular substituted heterocycle fused gamma-carboline compounds (the compounds described herein below) are effective in treating not just acute symptoms, but also residual symptoms of psychosis. Therefore, the invention provides methods of using the particular substituted heterocycle fused gamma-carboline compounds (the compounds described herein below), either alone or as an adjunctive therapy for the treatment of residual symptoms of psychosis, particularly schizophrenia.

US 2011/112105 discloses methods of preparing toluenesulfonic acid addition salt crystals of particular substituted heterocycle fused gamma-carbolines, e.g., toluenesulfonic acid addition salt of 4-((6bR,10a5)-3-methyl-2,3,6b,9,10,10a-hexahydro-1H-pyrido[3',4': 4,5]pyrrolo[1,2,3-de]quinoxalin-8(7H)-yl)-1-(4-fluorophenyl)-1-butanone.

US 2013/0202692 discloses prodrugs/metabolites of substituted heterocycle fused gamma-carboline for improved formulation, e.g., extended/controlled release formulation. This application discloses that heterocycle fused gamma-carboline N-substituted with a 4-fluorophenyl(4-hydroxy) butyl moiety are shown to have high selectivity for the serotonin transporter (SERT) relative to the heterocycle fused gamma-carboline containing 4-fluorophenylbutanone. The hydroxy group on these compounds, however, is inter-converted to and from the ketone within the plasma and the brain, allowing it to serve as a reservoir for the 4-fluorophenylbutanone drug. While substituted heterocycle fused gamma-carbolines and their uses are known, our inventors have surprisingly found that particular substituted heterocycle fused gamma-carbolines, while less active in in-vitro tests, are inter-converted between these less active compounds and the highly active ketone drug within the plasma and the brain. Our inventors have further provided prodrugs of particular substituted heterocycle fused gamma-carbolines that have altered pharmacokinetic profile, e.g., altered mechanisms and/or rate of absorption and distribution, and therefore may be useful for an improved formulation and/or for controlling the duration of the effect of the drug in the body (e.g., for sustained- or controlled release).

SUMMARY OF THE INVENTION

Applicants have unexpectedly discovered that the major routes of metabolism of fused heterocycle gamma carboline of Formula Q are by way of N-dealkylation and alpha-oxidation at the piperazine ring, and by reduction of the carbonyl, to yield the compounds of Formula Q-1, Q-2 and Q-3, as shown below:

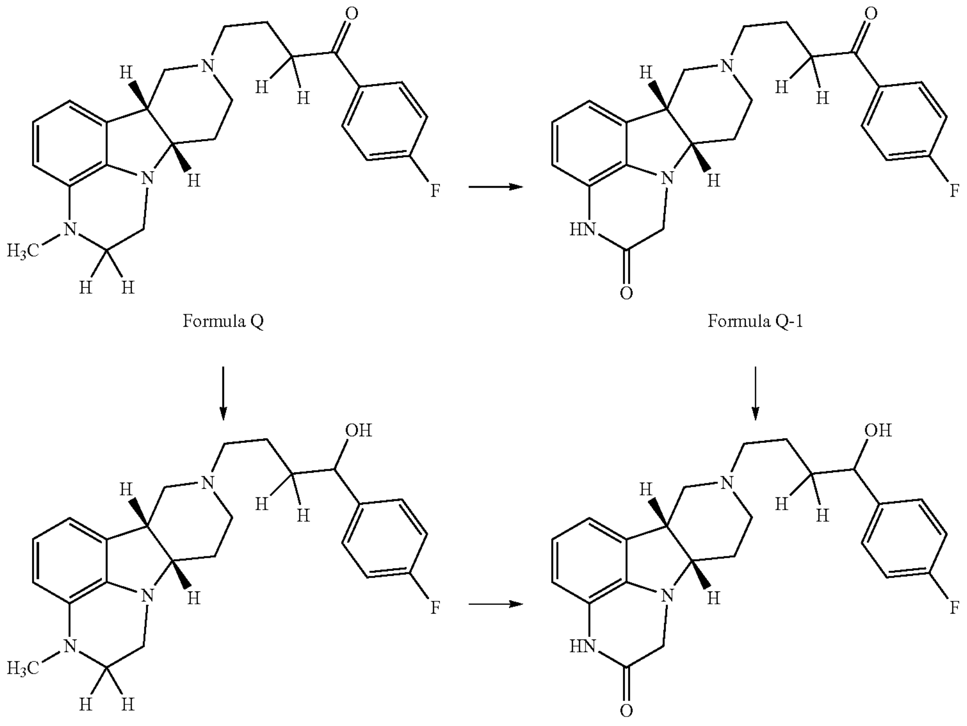

Formula Q Formula Q-1 Formula Q-2 Formula Q-3

US 2015/0079172 discloses compounds which block the in vivo inter-conversion between the hydroxy and the ketone, by incorporating an alkyl substituent on the carbon bearing the hydroxyl group, thus yielding compounds which antagonize 5-$HT_{2A}$ receptors and also inhibit serotonin re-uptake transporter.

The major routes of metabolism of the compounds previously disclosed are N-demethylation catalyzed by CYP 3A4, and ketone reduction catalyzed by ketone reductase. N-dealkylation by cytochrome oxidase enzymes is known to occur via an initial oxidation of one or more of the carbon atoms alpha to the nitrogen atom. The family of enzymes that catalyze ketone reduction is large and varied, and the mechanism has not been absolutely elucidated. It is of interest that, mechanistically, ketone reduction may operate either by way of the enol tautomer of the ketone or the keto tautomer.

US 2017/0183350 discloses generic deuterated heterocycle fused gamma carbolines for the purpose of reducing metabolic degradation by partially limiting metabolism of the ketone and/or the N-methyl substituent. Additionally, WO 2017/165843 discloses particular deuterated fused gamma carboline for the purpose of reducing metabolic degradation of said compounds. WO 2017/117514 (Tung et al.) further generically discloses deuterated compounds of this core.

Applicants have further found that the alcohol metabolite of Formula Q-2 retains significant pharmacological activity.

Without being bound by theory, the current invention provides compounds which specifically limit and/or prevent metabolism occurring by these pathways. Due to the very similar properties of deuterium ($^2H$) atoms compared to normal hydrogen atoms ($^1H$), drug compounds in which deuterium is substituted for hydrogen are believed to generally have similar biological activity to the non-deuterated analog, but potentially with improved pharmacokinetic properties. The extent to which such a substitution will result in an improvement of pharmacokinetic properties without a too severe loss in pharmacologic activity is variable. Thus, in some circumstances, the resulting deuterated compound only a moderate increase in pharmacokinetic stability, while in other circumstances, the resulting deuterated compound may have significantly improved stability. Moreover, it may be difficult to predict with certainty the effects of simultaneous deuterium substitutions. These may or may not result in additive (synergistic) improvement in metabolic stability.

The current invention provides compounds containing a trideuterated N-methyl, and/or a di-deuterated methylene adjacent to the N-methyl, along with a mono- or di-deuterated methylene adjacent to the opposite piperazine nitrogen. These novel compounds antagonize 5-$HT_{2A}$ receptors, inhibit the serotonin re-uptake transporter, and modulate dopaminergic protein phosphorylation, in a like manner as to their natural hydrogen analogs. However, these compounds display an unexpectedly improved metabolic stability.

In the first embodiment, the invention provides a compound of Formula I:

Formula I

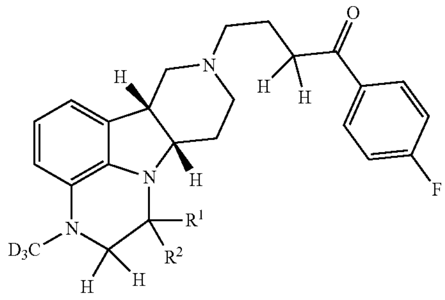

wherein at least one of $R^1$ and $R^2$, or both, is D, in free or salt form, e.g., in pharmaceutically acceptable salt form (e.g., tosylate).

In the second embodiment, the invention provides a compound of Formula II:

Formula II

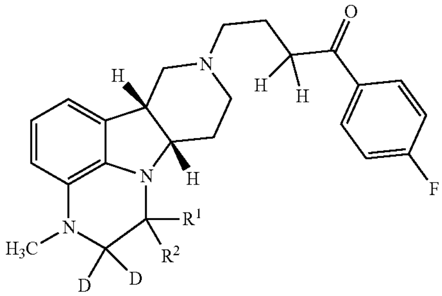

wherein at least one of $R^1$ and $R^2$, or both, is D, in free or salt form, e.g., in pharmaceutically acceptable salt form (e.g., tosylate).

In the third embodiment, the invention provides a compound of formula III:

Formula III

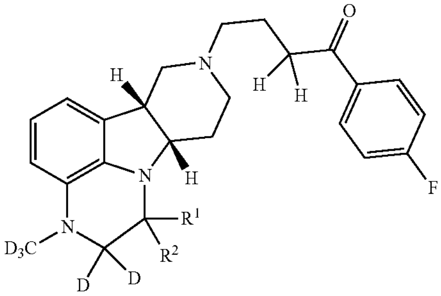

wherein at least one of $R^1$ and $R^2$, or both, is D, in free or salt form, e.g., in pharmaceutically acceptable salt form (e.g., tosylate).

In the fourth embodiment, the invention provides a compound of formula IV, in

Formula IV

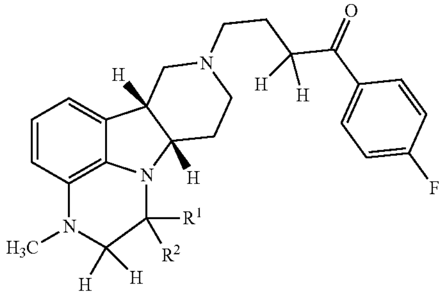

wherein at least one of $R^1$ and $R^2$, or both, is D, in free or salt form, e.g., in pharmaceutically acceptable salt form (e.g., tosylate).

In additional embodiments, the invention provides compounds as follows:

- 1.1 A compound of any of Formulas I to IV, wherein $R^1$ is H and $R^2$ is D;
- 1.2 A compound of any of Formulas I to IV, wherein $R^1$ and $R^2$ are both D;
- 1.3 A compound of any of Formulas I to IV, wherein the compound is in free or pharmaceutically acceptable salt form;
- 1.4 A compound of Formula 1.3, wherein the salt form is an acid addition salt of a pharmaceutically acceptable acid;
- 1.5 A compound of Formula 1.4 wherein the acid is toluenesulfonic acid, e.g., wherein the compound is a mono-tosylate, di-tosylate or tri-tosylate salt, or a mixture thereof;
- 1.6 A compound of any of Formulas I to IV or 1.1-1.5, wherein the Compound is in substantially pure diastereomeric form (i.e., substantially free from other diastereomers);
- 1.7 A compound of any of Formulas I to IV or 1.1-1.6, wherein the Compound has a diastereomeric excess of greater than 70%, preferably greater than 80%, more preferably greater than 90% and most preferably greater than 95%;
- 1.8 A compound of any of Formulas I to IV or 1.1-1.7, wherein the compound has greater than natural incorporation of deuterium at the indicated deuterium positions of the structure (i.e., greater than 0.0156%);
- 1.9 A compound of any of Formulas I to IV or 1.1-1.8, wherein the compound has substantially greater than natural incorporation of deuterium at the indicated deuterium positions of the structure (e.g., greater than 0.1%, or greater than 0.5%, or greater than 1%, or greater than 5%);
- 1.10 A compound of any of Formulas I to IV or 1.1-1.9, wherein the compound has greater than 50% incorporation of deuterium at the indicated deuterated positions of the structure (i.e., greater than 50 atom % D), e.g., greater than 60%, or greater than 70%, or greater than 80%, or greater than 90% or greater than 95%, or greater than 96%, or greater than 97%, or greater than 98%, or greater than 99%.

In a second aspect, the invention provides a pharmaceutical composition (Pharmaceutical Composition 2) comprising the compound of any of Formulas I to IV or 1.1-1.10 (hereinafter the Compounds of the Invention), in free or pharmaceutically acceptable salt form, in admixture with a pharmaceutically acceptable diluent or carrier, e.g. to provide immediate release or to provide sustained or delayed release. The present disclosure provides additional exemplary embodiments of Pharmaceutical Composition 2, including:

- 2.1 Pharmaceutical Composition 2, wherein the Compound of Formula I et seq. is in solid form;
- 2.2 Pharmaceutical Composition 2 or 2.1, wherein the Compound of Formulas I et seq. is in pharmaceutically acceptable salt form as described in any of Compounds 1.1-1.10;
- 2.3 Pharmaceutical Composition 2, or any of 2.1-2.2, wherein the composition is a depot formulation, as described herein (e.g., wherein the composition is formulated as a long-acting injectable, for example, for intramuscular or subcutaneous injection).
- 2.4 Pharmaceutical Composition 2, or any of 2.1-2.3, wherein the compound of Formula I et seq. is in a polymeric matrix.

In a further embodiment of the second aspect, the Pharmaceutical Composition of the Invention (e.g., Pharmaceutical Composition 2 or 2.1-2.4) is for a sustained or delayed release, e.g., a depot formulation. In one embodiment, the depot formulation comprises the Compounds of the Invention in a polymeric matrix. In another embodiment, the Compounds of the Invention are dispersed or dissolved within the polymeric matrix. In a further embodiment, the polymeric matrix comprises standard polymers used in depot formulations such as polymers selected from a polyester of a hydroxy fatty acid and derivatives thereof, or a polymer of an alkyl alpha-cyanoacrylate, a polyalkylene oxalate, a poly(ortho ester), a polycarbonate, a polyorthocarbonate, a poly(amino acid), a hyaluronic acid ester, and mixtures thereof. In a further embodiment, the polymer is selected from a group consisting of polylactide, poly d,l-lactide, poly glycolide, PLGA 50:50, PLGA 75:25, PLGA 85:15 and PLGA 90:10 polymer. In another embodiment, the polymer is selected from poly(glycolic acid), poly-D,L-lactic acid, poly-L-lactic acid, copolymers of the foregoing, poly(aliphatic carboxylic acids), copolyoxalates, polycaprolactone, polydioxonone, poly(ortho carbonates), poly(acetals), poly(lactic acid-caprolactone), polyorthoesters, poly (glycolic acid-caprolactone), polyanhydrides, and natural polymers including albumin, casein, and waxes, such as, glycerol mono- and distearate, and the like. In a particular embodiment, the polymeric matrix comprises poly (d,l-lactide-co-glycolide). Any of the Compositions hereinbefore described may be a pharmaceutical composition wherein said composition is in admixture with a pharmaceutically acceptable diluent or carrier.

The (Pharmaceutical) depot formulations as hereinbefore described are particularly useful for sustained or delayed release, wherein the Compounds of the Invention are released upon degradation of the polymeric matrix. These Compositions may be formulated for controlled- and/or sustained-release of the Compounds of the Invention (e.g., as a depot composition) over a period of up to 180 days, e.g., from about 14 to about 30 to about 180 days. For example, the polymeric matrix may degrade and release the Compounds of the Invention over a period of about 30, about 60 or about 90 days. In another example, the polymeric matrix may degrade and release the Compounds of the Invention over a period of about 120, or about 180 days.

In still another further embodiment, the Pharmaceutical Compositions of the Invention (e.g., Pharmaceutical Composition 2 or 2.1-2.4), particularly the depot compositions of the Invention, are formulated for administration by injection.

In a third aspect, the invention provides the Compounds of the Invention (e.g., Compounds I-IV and 1.1-1.10) as hereinbefore described in an oral sustained or delayed release formulation. For example, the invention provides an osmotic controlled release oral delivery system (OROS) for delivery of the Compounds of the Invention, e.g. analogous to the systems described in WO 2000/35419 and EP 1 539 115 (U.S. Pub. No. 2009/0202631), the contents of each of which applications are incorporated by reference in their entirety. Therefore in one embodiment of this aspect, the invention provides a pharmaceutical composition or device comprising (a) a gelatin capsule containing a Compound of the Invention in free or pharmaceutically acceptable salt form or a Pharmaceutical Composition of the Invention (e.g., Pharmaceutical Composition 2 or 2.1-2.4), as hereinbefore described; (b) a multilayer wall superposed on the gelatin capsule comprising, in outward order from the capsule: (i) a barrier layer, (ii) an expandable layer, and (iii) a semipermeable layer; and (c) and orifice formed or formable through the wall. (Pharmaceutical Composition P.1).

In another embodiment of this aspect, the invention provides a composition comprising a gelatin capsule containing a liquid, the Compounds of the Invention in free or pharmaceutically acceptable salt form or a Pharmaceutical Composition of the Invention (e.g., Pharmaceutical Composition 2 or 2.1-2.4) as hereinbefore described, the gelatin capsule being surrounded by a composite wall comprising a barrier layer contacting the external surface of the gelatin capsule, an expandable layer contacting the barrier layer, a semi-permeable layer encompassing the expandable layer, and an exit orifice formed or formable in the wall. (Pharmaceutical Composition P.2)

In still another embodiment of the third aspect, the invention provides a composition comprising a gelatin capsule containing a liquid, the Compound of the Invention in free or pharmaceutically acceptable salt form or a Pharmaceutical Composition of the Invention (e.g., Pharmaceutical Composition 2 or 2.1-2.4) as hereinbefore described, the gelatin capsule being surrounded by a composite wall comprising a barrier layer contacting the external surface of the gelatin capsule, an expandable layer contacting the barrier layer, a semipermeable layer encompassing the expandable layer, and an exit orifice formed or formable in the wall, wherein the barrier layer forms a seal between the expandable layer and the environment at the exit orifice. (Pharmaceutical Composition P.3)

In still another embodiment of the third aspect, the invention provides a composition comprising a gelatin capsule containing a liquid, the Compound of the Invention in free or pharmaceutically acceptable salt form or a Pharmaceutical Composition of the Invention (e.g., Pharmaceutical Composition 2 or 2.1-2.4) as hereinbefore described, the gelatin capsule being surrounded by a barrier layer contacting the external surface of the gelatin capsule, an expandable layer contacting a portion of the barrier layer, a semi-permeable layer encompassing at least the expandable layer, and an exit orifice formed or formable in the dosage form extending from the external surface of the gelatin capsule to the environment of use. (Pharmaceutical Composition P.4). The expandable layer may be formed in one or more discrete sections, such as for example, two sections located on opposing sides or ends of the gelatin capsule.

In a particular embodiment of the third aspect, the Compound of the Inventions in the Osmotic-controlled Release Oral Delivery System (i.e., in Pharmaceutical Composition P.1-P.4) are in a liquid formulation, which formulation may be neat, liquid active agent, liquid active agent in a solution, suspension, emulsion or self-emulsifying composition or the like.

Further information on Osmotic-controlled Release Oral Delivery System composition including characteristics of the gelatin capsule, barrier layer, an expandable layer, a semi-permeable layer; and orifice may be found in WO 2000/35419, the contents of which are incorporated by reference in their entirety. Other Osmotic-controlled Release Oral delivery System for the Compound or the Pharmaceutical Composition of the Invention may be found in EP 1 539 115 (U.S. Pub. No. 2009/0202631), the contents of which are incorporated by reference in their entirety.

Therefore, in another embodiment of the third aspect, the invention provides a composition or device comprising (a) two or more layers, said two or more layers comprising a first layer and a second layer, said first layer comprises the Compound of the Invention, in free or pharmaceutically acceptable salt form, or a Pharmaceutical Composition (e.g., Pharmaceutical Composition 2 or 2.1-2.4) as herein before described said second layer comprises a polymer; (b) an outer wall surrounding said two or more layers; and (c) an orifice in said outer wall. (Pharmaceutical Composition P.5)

Composition P.5 preferably utilizes a semi-permeable membrane surrounding a three-layer-core: in these embodiments the first layer is referred to as a first drug layer and contains low amounts of drug (e.g., the Compounds of the Invention) and an osmotic agent such as salt, the middle layer referred to as the second drug layer contains higher amounts of drug, excipients and no salt; and the third layer referred to as the push layer contains osmotic agents and no drug. At least one orifice is drilled through the membrane on the first drug layer end of the capsule-shaped tablet. (Pharmaceutical Composition P.6)

Pharmaceutical Composition P.5 or P.6 may comprise a membrane defining a compartment, the membrane surrounding an inner protective subcoat, at least one exit orifice formed or formable therein and at least a portion of the membrane being semi-permeable; an expandable layer located within the compartment remote from the exit orifice and in fluid communication with the semi-permeable portion of the membrane; a first drug layer located adjacent the exit orifice; and a second drug layer located within the compartment between the first drug layer and the expandable layer, the drug layers comprising the Compound of the Invention in free or pharmaceutically acceptable salt thereof. Depending upon the relative viscosity of the first drug layer and second drug layer, different release profiles are obtained. It is imperative to identify the optimum viscosity for each layer. In the present invention, viscosity is modulated by addition of salt, sodium chloride. The delivery profile from the core is dependent on the weight, formulation and thickness of each of the drug layers.

In a particular embodiment, the invention provides Pharmaceutical Composition P.7, wherein the first drug layer comprising salt and the second drug layer containing no salt. Pharmaceutical Composition P.5-P.7 may optionally comprise a flow-promoting layer between the membrane and the drug layers. Pharmaceutical Compositions P.1-P.7 will generally be referred to as Osmotic-controlled Release Oral Delivery System Composition.

In a fourth aspect, the invention provides a method (Method I) for the treatment or prophylaxis of a central nervous system disorder, comprising administering to a patient in need thereof, a compound of Formulas Ito IV or 1.1-1.10, in free or pharmaceutically acceptable salt form, or a pharmaceutical composition as hereinbefore described (e.g., Pharmaceutical Composition 2 or 2.1-2.4 or P.1-P.7), and optionally wherein the compound of Formulas Ito IV or 1.1-1.10 is administered in an effective dose which is lower than the effective dose for treatment of the same disorder using the compound of Formula Q.

In a further embodiment of the fourth aspect, the invention provides Method I wherein the method is further as described in the following formulae:

- 7.1 Method I, wherein the central nervous system disorder is one or more disorders associated with dementia, e.g., disorders associated with mild cognition impairment and dementing illnesses including senile dementia, Alzheimer's disease, Pick's disease, fronto-temporal dementia, parasupranuclear palsy, dementia with Lewy bodies, vascular dementia, Huntington's disease, Parkinson's disease, multiple sclerosis, amyotrophic lateral sclerosis, Down syndrome, elderly depression, Wernicke-Korsakoff's syndrome, cortico-basal degenerations and prion disease, autism and attention deficit hyperactivity disorder;
- 7.2 Method I or 7.1, wherein the disorders associated with dementia is selected from the group consisting of (1) behavioral or mood disorders such as agitation/irritation, aggressive/assaultive behavior, anger, physical or emotional outbursts; (2) psychosis; (3) depression; and (4) sleep disorders;
- 7.3 Method I or 7.1, wherein the central nervous system disorder is agitation/irritation, aggressive/assaultive behavior, anger, physical or emotional outbursts;
- 7.4 Method I, wherein the central nervous system disorder is a disorder selected from a group consisting of obesity, anxiety, depression (for example refractory depression and Major Depressive Disorder (MDD)), psychosis, schizophrenia, sleep disorders (particularly sleep disorders associated with schizophrenia and other psychiatric and neurological diseases), sexual disorders, migraine, conditions associated with cephalic pain, social phobias, agitation in dementia (e.g., agitation in Alzheimer's disease), agitation in autism and related autistic disorders, and gastrointestinal disorders such as dysfunction of the gastrointestinal tract motility;
- 7.5 Method I or any of 7.2-7.4, wherein the central nervous system disorder is a disorder involving serotonin 5-$HT_{2A}$, dopamine $D_1/D_2$ receptor system and/or serotonin reuptake transporter (SERT) pathways as similarly described in WO/2009/145900, the contents of which are herein incorporated by reference in their entirety;
- 7.6 Method I or any of Formulae 7.2-7.5, wherein the central nervous system disorder is a disorder involving serotonin reuptake transporter (SERT) pathways;
- 7.7 Method I or any of Formulae 7.2-7.6, wherein the central nervous system disorder is a disorder selected from the following: (i) psychosis, e.g., schizophrenia, in a patient suffering from depression; (2) depression in a patient suffering from psychosis, e.g., schizophrenia; (3) mood disorders associated with psychosis, e.g., schizophrenia or Parkinson's disease; and (4) sleep disorders associated with psychosis, e.g., schizophrenia or Parkinson's disease; (5) depression; (6) anxiety; (7) post-traumatic stress disorder; or (8) impulse control disorder, e.g., intermittent explosive disorder;
- 7.8 Method I or any of Formulae 7.2-7.7, wherein the central nervous system disorder is psychosis, e.g., schizophrenia and said patient is a patient suffering from depression;

7.9 Method I or any of Formulae 7.2-7.8, wherein said patient is unable to tolerate the side effects of conventional antipsychotic drugs, e.g., chlorpromazine, haloperidol, droperidol, fluphenazine, loxapine, mesoridazine, molindone, perphenazine, pimozide, prochlorperazine, promazine, thioridazine, thiothixene, trifluoperazine, brexpiprazole, cariprazine, asenapine, lurasidone, clozapine, aripiprazole, olanzapine, quetiapine, risperidone and ziprasidone;

7.10 Method I or any of Formulae 7.2-7.9, wherein said patient is unable to tolerate the side effects of conventional antipsychotic drugs, e.g., haloperidol, aripiprazole, clozapine, olanzapine, quetiapine, risperidone, and ziprasidone;

7.11 Method I or any of Formulae 7.2-7.10, wherein said disorder is depression and said patient is a patient suffering from psychosis, e.g., schizophrenia, or Parkinson's disease;

7.12 Method I or any of Formulae 7.2-7.6, wherein said disorder is sleep disorder and said patient is suffering from depression;

7.13 Method I or any of 7.2-7.6, wherein said one or more disorders is sleep disorder and said patient is suffering from psychosis, e.g., schizophrenia;

7.14 Method I or any of 7.2-7.6, wherein said one or more disorders is sleep disorder and said patient is suffering from Parkinson's disease;

7.15 Method I or any of 7.2-7.6, wherein said one or more disorders is sleep disorder and said patient is suffering from depression and psychosis, e.g., schizophrenia, or Parkinson's disease;

7.16 Method I or any of 7.1-7.6, wherein the central nervous system disorder is residual symptoms of psychosis, for example, schizophrenia (e.g., residual subtype), delusional disorder (e.g., somatic type), major depression with psychosis, bipolar disorder with psychotic symptoms, brief psychotic disorder, schizophreniform disorder, schizoaffective disorder or psychosis caused by a medical condition or substance use. Preferably, the patient is suffering from residual symptoms of schizophrenia;

7.17 Method I or any of 7.1-7.6, wherein the residual phase symptoms include: negative symptoms such as blunted affect, emotional withdrawal, poor rapport, passive or apathetic social withdrawal, difficulty in abstract thinking, lack of spontaneity and flow of conversation and stereotyped thinking; general psychopathology symptoms such as somatic concern, anxiety, guilt feelings, tension, mannerisms and posturing, depression, motor retardation, uncooperativeness, unusual thought content, disorientation, poor attention, lack of judgment and insight, disturbance of volition, poor impulse control, preoccupation and active social avoidance; cognitive impairment and sleep disorders (e.g., insomnia);

7.18 Any of the foregoing methods, wherein the effective amount is 1 mg-1000 mg, preferably 2.5 mg-50 mg, still preferably 1-40 mg, e.g., 1-10 mg, e.g., 10 mg, 20 mg, or greater than 20 mg, e.g., 30 mg, 40 mg;

7.19 Any of the foregoing methods, wherein the effective amount is 1 mg-100 mg per day, preferably 2.5 mg-50 mg per day, still preferably 1-40 mg/day, e.g., 1-10 mg/day, e.g., 10 mg/day, 20 mg/day, or greater than 20 mg/day, e.g., 30 mg/day, 40 mg/day;

7.20 Any of the foregoing methods wherein a condition to be treated is dyskinesia, e.g. in a patient receiving dopaminergic medications, e.g., medications selected from levodopa and levodopa adjuncts (carbidopa, COMT inhibitors, MAO-B inhibitors), dopamine agonists, e.g., levodopa, and anticholinergics;

7.21 Any of the foregoing methods wherein the patient suffers from Parkinson's disease;

7.22 Any of the foregoing methods wherein the patient does not respond to a selective serotonin re-uptake inhibitor, e.g. selected from one or more of citalopram (Celexa, Cipramil, Cipram, Dalsan, Recital, Emocal, Sepram, Seropram, Citox, Cital); dapoxetine (Priligy); escitalopram (Lexapro, Cipralex, Seroplex, Esertia); fluoxetine (Depex, Prozac, Fontex, Seromex, Seronil, Sarafem, Ladose, Motivest, Flutop, Fluctin (EUR), Fluox (NZ), Depress (UZB), Lovan (AUS), Prodep (IND)); fluvoxamine (Luvox, Fevarin, Faverin, Dumyrox, Favoxil, Movox); indalpine (Upstene); paroxetine (Paxil, Seroxat, Sereupin, Aropax, Deroxat, Divarius, Rexetin, Xetanor, Paroxat, Loxamine, Deparoc); sertraline (Zoloft, Lustral, Serlain, Asentra); vilazodone (Viibryd); or zimelidine (Zelmid, Normud);

7.23 Any of the foregoing methods wherein the patients is also receiving a selective serotonin re-uptake inhibitor, e.g. selected from one or more of citalopram (Celexa, Cipramil, Cipram, Dalsan, Recital, Emocal, Sepram, Seropram, Citox, Cital); dapoxetine (Priligy); escitalopram (Lexapro, Cipralex, Seroplex, Esertia); fluoxetine (Depex, Prozac, Fontex, Seromex, Seronil, Sarafem, Ladose, Motivest, Flutop, Fluctin (EUR), Fluox (NZ), Depress (UZB), Lovan (AUS), Prodep (IND)); fluvoxamine (Luvox, Fevarin, Faverin, Dumyrox, Favoxil, Movox); indalpine (Upstene); paroxetine (Paxil, Seroxat, Sereupin, Aropax, Deroxat, Divarius, Rexetin, Xetanor, Paroxat, Loxamine, Deparoc); sertraline (Zoloft, Lustral, Serlain, Asentra); vilazodone (Viibryd); or zimelidine (Zelmid, Normud);

7.24 Any of the foregoing methods wherein the patients is suffering from autistic spectrum disorder, e.g., autism or Asperger Syndrome;

7.25 Any of the foregoing methods wherein the patients is suffering from dementia, e.g., disorders associated with mild cognition impairment and dementing illnesses including senile dementia, Alzheimer's disease, Pick's disease, fronto-temporal dementia, parasupranuclear palsy, dementia with Lewy bodies, vascular dementia, Huntington's disease, Parkinson's disease, multiple sclerosis, amyotrophic lateral sclerosis, Down syndrome, elderly depression, Wernicke-Korsakoff s syndrome, cortico-basal degenerations and prion disease, autism and attention deficit hyperactivity disorder;

7.26 Any of the foregoing methods wherein the patient is also receiving a cholinesterase inhibitor (e.g., acetylcholinesterase inhibitor) or an N-Methyl D-Aspartate (NMDA) receptor antagonist, in free or pharmaceutically acceptable salt form;

7.27 Method 7.26, wherein the cholinesterase inhibitor (e.g., acetylcholinesterase inhibitor) is selected from the group consisting of Tacrine, rivastigmine (Exelon), donepezil (Aricept), and galantamine (Razadyne, formerly called Reminyl)) in free or pharmaceutically acceptable salt form;

7.28 Method 7.26, wherein the cholinesterase inhibitor (e.g., acetylcholinesterase inhibitor) is donepezil in free or pharmaceutically acceptable salt form;

7.29 Method 7.26, wherein the NMDA receptor antagonist is memantine in free or pharmaceutically acceptable salt form;

7.30 Any of the foregoing methods further comprising administering one or more other therapeutic agents such as additional antipsychotic agents and/or anti-depressive agents and/or hypnotic agents;

7.31 Method 7.30, wherein the one or more other therapeutic agents are selected from anti-depressive agents such as compounds that modulate GABA activity (e.g., enhances the activity and facilitates GABA transmission), a GABA-B agonist, a 5-HT modulator (e.g., a 5-HT1A agonist, a 5-HT2A antagonist, a 5-HT2A inverse agonist, etc.), a melatonin agonist, an ion channel modulator (e.g., blocker), a serotonin-2 receptor antagonist/reuptake inhibitor (SARIs), an orexin receptor antagonist, an H3 agonist, a noradrenergic antagonist, a galanin agonist, a CRH antagonist, human growth hormone, a growth hormone agonist, estrogen, an estrogen agonist, a neurokinin-1 drug; and antipsychotic agents, e.g., atypical antipsychotic agents, in free or pharmaceutically acceptable salt form;

7.32 Method 7.30 or 7.31, wherein the one or more other therapeutic agents are antipsychotic agents, e.g., chlorpromazine, haloperidol, droperidol, fluphenazine, loxapine, mesoridazine, molindone, perphenazine, pimozide, prochlorperazine promazine, thioridazine, thiothixene, trifluoperazine, brexpiprazole, cariprazine, asenapine, lurasidone, clozapine, aripiprazole, olanzapine, quetiapine, risperidone, ziprasidone, paliperidone, asenapine, lurasidone, iloperidone, cariprazine, amisulpride, zotepine, sertindole, wherein the one or more other therapeutic agents are administered as an adjunct to the compound of Formulas Ito IV or 1.1-1.10 or the compound of Formulas Ito IV or 1.1-1.10 is an adjunct to the one or more other therapeutic agents.

In a particular embodiment of the fourth aspect, the invention provides a method (Method $I_P$) for the treatment or prophylaxis of a central nervous system disorder as hereinbefore described, comprising administering to a patient in need thereof:

7.4P a compound of Formulas I to IV or 1.1-1.10, in free or pharmaceutically acceptable salt form;

7.8P a Pharmaceutical or Depot Composition as hereinbefore described (e.g., Pharmaceutical Composition 2 or 2.1-2.4 or P.1-P.7); or 7.11P Osmotic-controlled Release Oral Delivery System Composition as hereinbefore described.

In a further embodiment of the fourth aspect, the invention provides Method $I_P$, wherein the method is further described in any one of formulae 7.1-7.32.

In a particular embodiment of the fourth aspect, the invention provides Method I, $I_P$, or any of 7.1-7.32, wherein the disorder is schizophrenia or sleep disorder.

In a particular embodiment of the fourth aspect, the invention provides Method I, $I_P$, or any of 7.1-7.32, wherein the disorder is depression or anxiety.

In a particular embodiment of the fourth aspect, the invention provides Method I, $I_P$, or any of 7.1-7.32, wherein the disorder is post-traumatic stress disorder or an impulse control disorder, e.g., intermittent explosive disorder.

In a particular embodiment of the fourth aspect, the invention provides Method I, $I_P$, or any of 7.1-7.32, wherein the disorder is post-traumatic stress disorder or an impulse control disorder, e.g., intermittent explosive disorder in a patient suffering from dementia, e.g., senile dementia, Alzheimer's disease, Pick's disease, fronto-temporal dementia, parasupranuclear palsy, dementia with Lewy bodies, vascular dementia, Huntington's disease, Parkinson's disease, multiple sclerosis, amyotrophic lateral sclerosis, Down syndrome, elderly depression, Wernicke-Korsakoffs syndrome, cortico-basal degenerations, prion disease, autism and/or attention deficit hyperactivity disorder.

In still another embodiment of the fourth aspect, the invention provides Method I, $I_P$, or any of 7.1-7.32, wherein the Depot Composition of the Invention is administered for controlled- and/or sustained-release of the Compounds of the Invention over a period of from about 14 days, about 30 to about 180 days, preferably over the period of about 30, about 60 or about 90 days. Controlled- and/or sustained-release is particularly useful for circumventing premature discontinuation of therapy, particularly for antipsychotic drug therapy where non-compliance or non-adherence to medication regimes is a common occurrence.

In a fifth aspect, the invention provides a method (Method II) for the prophylaxis or treatment one or more sleep disorders, agitation, aggressive behaviors, post-traumatic stress disorder and/or impulse control disorder, e.g., intermittent explosive disorder, comprising administering to a patient in need thereof a compound as described in the following formulae:

8.1 a compound of Formulas Ito IV or 1.1-1.10, in free or pharmaceutically acceptable salt form;

8.2 a Pharmaceutical or Depot Composition as hereinbefore described (e.g., Pharmaceutical Composition 2 or 2.1-2.4 or P.1-P.7);

8.3 Osmotic-controlled Release Oral Delivery System Composition as hereinbefore described.

In one embodiment of the fifth aspect, the invention provides Method II or any of 8.1-8.3, wherein the disorder is sleep disorders. In another embodiment of the fifth aspect, the invention provides Method II, wherein the disorder is agitation, aggressive behaviors, post-traumatic stress disorder and/or impulse control disorder, e.g., intermittent explosive disorder.

In a further embodiment of the fifth aspect, the invention provides Method II, 8.1-8.3, wherein the sleep disorder includes sleep maintenance insomnia, frequent awakenings, and waking up feeling unrefreshed;

8.4 Any of the foregoing methods, wherein the sleep disorder is sleep maintenance insomnia;

8.5 Any of the foregoing methods, wherein the effective amount is 1 mg-10 mg per day, e.g., 1-5 mg, preferably 2.5-5 mg, per day, still preferably 10 mg per day;

8.6 Any of the foregoing methods, wherein the effective amount is 2.5 mg or 5 mg, per day or 10 mg per day;

8.7 Any of the foregoing methods wherein the sleep disorder is in a patient suffering from or at risk of dyskinesia, e.g., a patient receiving dopaminergic medications, e.g., selected from levodopa and levodopa adjuncts (carbidopa, COMT inhibitors, MAO-B inhibitors), dopamine agonists, e.g., receiving levodopa, and anticholinergics;

8.8 Any of the foregoing methods wherein the patient suffers from Parkinson's disease.

The Compounds of the Invention (e.g., a compound of Formulas I to IV or 1.1-1.10) provide effective treatment of 5-$HT_{2A}$, SERT and/or $D_2$ receptor related disorders without or with minimal extrapyramidal side effects as similarly disclosed and claimed in WO 2009/145900, the contents of which are incorporated by reference in their entirety. Therefore, the Compounds of the Invention, the Pharmaceutical Compositions of the Invention or the Depot Compositions of the Invention may be used in combination with a second therapeutic agent, particularly at lower dosages than when the individual agents are used as a monotherapy so as to enhance the therapeutic activities of the combined agents without causing the undesirable side effects commonly occur in conventional monotherapy. Therefore, the Compounds of the Invention may be simultaneously, sequentially, or contemporaneously administered with other anti-depressant, anti-psychotic, other hypnotic agents, and/or agents use to treat Parkinson's disease or mood disorders or dementia. In another example, side effects may be reduced or minimized by administering a Compound of the Invention in combination with one or more second therapeutic agents in free or salt form, wherein the dosages of (i) the second therapeutic agent(s) or (ii) both Compound of the Invention and the second therapeutic agent, are lower than if the agent/compound are administered as a monotherapy. In a particular embodiment, the Compounds of the Invention are useful to treat dyskinesia in a patient receiving dopaminergic medications, e.g., selected from levodopa and levodopa adjuncts (carbidopa, COMT inhibitors, MAO-B inhibitors), dopamine agonists, e.g., such as are used in the treatment of Parkinson's disease, and anticholinergics used to treat side effects of Parkinson's disease medications.

Therefore, in a sixth aspect, the current invention provides Method I or $I_P$, e.g., or any of formulae 7.1-7.32, or Method II or any of 8.1-8.8, wherein the method further comprises the administration to the patient of one or more therapeutic agents selected from compounds that modulate GABA activity (e.g., enhances the activity and facilitates GABA transmission), a GABA-B agonist, a 5-HT modulator (e.g., a 5-$HT_{1A}$ agonist, a 5-$HT_{2A}$ antagonist, a 5-$HT_{2A}$ inverse agonist, etc.), a melatonin agonist, an ion channel modulator (e.g., blocker), a serotonin-2 receptor antagonist/reuptake inhibitor (a compound having both 5-$HT_2$ antagonism and serotonin reuptake inhibition, i.e., SARIs), an orexin receptor antagonist, an H3 agonist or antagonist, a noradrenergic agonist or antagonist, a galanin agonist, a CRH antagonist, human growth hormone, a growth hormone agonist, estrogen, an estrogen agonist, a neurokinin-1 drug, an anti-depressant, and an antipsychotic agent, e.g., an atypical antipsychotic agent, in free or pharmaceutically acceptable salt form (Method I-A and II-A respectively).

In another embodiment of the sixth aspect, Method I-A and II-A, Method I, Method $I_P$, e.g., or any of formulae 7.1-7.32, or Method II or any of 8.1-8.8, further comprises the administration to a patient of one or more therapeutic agents selected from a cholinesterase inhibitor (e.g., acetyl-cholinesterase inhibitor) or an N-Methyl D-Aspartate (NMDA) receptor antagonist, in free or pharmaceutically acceptable salt form. In a specific embodiment, the cholinesterase inhibitor (e.g., acetylcholinesterase inhibitor) is selected from the group consisting of Tacrine, rivastigmine (Exelon), donepezil (Aricept), and galantamine (Razadyne, formerly called Reminyl)) in free or pharmaceutically acceptable salt form. In a further embodiment, the cholinesterase inhibitor (e.g., acetylcholinesterase inhibitor) is donepezil in free or pharmaceutically acceptable salt form. In another embodiment, the NMDA receptor antagonist is memantine in free or pharmaceutically acceptable salt form.

In a further embodiment of the sixth aspect, the invention provides Method I-A or II-A as follows, further comprising the administration to the patient of one or more therapeutic agents, as follows:

9.1 Method I-A or II-A, wherein the therapeutic agent(s) is compounds that modulate GABA activity (e.g., enhances the activity and facilitates GABA transmission);

9.2 Method I-A or II-A or 9.1, wherein the GABA compound is selected from a group consisting of one or more of doxepin, alprazolam, bromazepam, clobazam, clonazepam, clorazepate, diazepam, flunitrazepam, flurazepam, lorazepam, midazolam, nitrazepam, oxazepam, temazapam, triazolam, indiplon, zopiclone, eszopiclone, zaleplon, Zolpidem, gabaxadol, vigabatrin, tiagabine, EVT 201 (Evotec Pharmaceuticals) and estazolam;

9.3 Method I-A or II-A, wherein the therapeutic agent is an additional $5HT_{2A}$ receptor antagonist;

9.4 Method I-A or II-A or 9.3, wherein said additional $5HT_{2A}$ receptor antagonist is selected from one or more of pimavanserin, ketanserin, risperidone, eplivanserin, volinanserin (Sanofi-Aventis, France), pruvanserin, MDL 100907 (Sanofi-Aventis, France), HY 10275 (Eli Lilly), APD 125 (Arena Pharmaceuticals, San Diego, CA), and AVE8488 (Sanofi-Aventis, France); Method I-A or II-A, 9.3 or 9.4 additionally selected from pimavanserin (ACP-103) and pizotifen;

9.5 Method I-A or II-A, wherein the therapeutic agent is a melatonin agonist;

9.6 Method I-A or II-A or 9.5, wherein the melatonin agonist is selected from a group consisting of one or more of melatonin, ramelteon (ROZEREM®, Takeda Pharmaceuticals, Japan), VEC-162 (Vanda Pharmaceuticals, Rockville, MD), PD-6735 (Phase II Discovery) and agomelatine;

9.7 Method I-A or II-A, wherein the therapeutic agent is an ion channel blocker;

9.8 Method I-A or II-A or 9.7, wherein said ion channel blocker is one or more of lamotrigine, gabapentin and pregabalin.

9.9 Method I-A or II-A, wherein the therapeutic agent is an orexin receptor antagonist;

9.10 Method I-A or II-A or 9.9, wherein the orexin receptor antagonist is selected from a group consisting of orexin, a 1,3-biarylurea, SB-334867-a (GlaxoSmithKline, UK), GW649868 (GlaxoSmithKline) and a benzamide derivative;

9.11 Method I-A or II-A, wherein the therapeutic agent is the serotonin-2 receptor antagonist/reuptake inhibitor (SARI);

9.12 Method I-A or II-A or 9.11, wherein the serotonin-2 receptor antagonist/reuptake inhibitor (SARI) is selected from a group consisting of one or more Org 50081 (Organon-Netherlands), ritanserin, nefazodone, serzone and trazodone;

9.13 Method I-A or II-A, wherein the therapeutic agent is the 5HT1a agonist;

9.14 Method I-A or II-A or 9.13, wherein the $5HT_{1a}$ agonist is selected from a group consisting of one or more of repinotan, sarizotan, eptapirone, buspirone and MN-305 (MediciNova, San Diego, CA);

9.15 Method I-A or II-A, wherein the therapeutic agent is the neurokinin-1 drug;

9.16 Method I-A or II-A or 9.15, wherein the neurokinin-1 drug is Casopitant (GlaxoSmithKline);

9.17 Method I-A or II-A, wherein the therapeutic agent is an antipsychotic agent;

9.18 Method I-A or II-A or 9.17, wherein the antipsychotic agent is selected from a group consisting of chlorpromazine, haloperidol, droperidol, fluphenazine, loxapine, mesoridazine, molindone, perphenazine, pimozide, prochlorperazine promazine, thioridazine, thiothixene, trifluoperazine, clozapine, brexpiprazole, cariprazine, asenapine, lurasidone, aripiprazole, olanzapine, quetiapine, risperidone, ziprasidone and paliperidone;

9.19 Method I-A or II-A, wherein the therapeutic agent is an anti-depressant;

9.20 Method I-A or II-A or 9.19, wherein the anti-depressant is selected from amitriptyline, amoxapine, bupropion, citalopram, clomipramine, desipramine, doxepin, duloxetine, escitalopram, fluoxetine, fluvoxamine, imipramine, isocarboxazid, maprotiline, mirtazapine, nefazodone, nortriptyline, paroxetine, phenelazine sulfate, protriptyline, sertraline, tranylcypromine, trazodone, trimipramine, and venlafaxine;

9.21 Method I-A or II-A, 9.17 or 9.18, wherein the antipsychotic agent is an atypical antipsychotic agent;

9.22 Method I-A or II-A, or any of 9.17-9.21, wherein the atypical antipsychotic agent is selected from a group consisting of brexpiprazole, cariprazine, asenapine, lurasidone, clozapine, aripiprazole, olanzapine, quetiapine, risperidone, ziprasidone, and paliperidone;

9.23 Method I-A or II-A, wherein the therapeutic agent is selected from any of methods 9.1-9.22, e.g., selected from a group consisting of modafinil, armodafinil, doxepin, alprazolam, bromazepam, clobazam, clonazepam, clorazepate, diazepam, flunitrazepam, flurazepam, lorazepam, midazolam, nitrazepam, oxazepam, temazapam, triazolam, indiplon, zopiclone, eszopiclone, zaleplon, Zolpidem, gabaxadol, vigabatrin, tiagabine, EVT 201 (Evotec Pharmaceuticals), estazolam, pimavanserin, ketanserin, risperidone, eplivanserin, volinanserin (Sanofi-Aventis, France), pruvanserin, MDL 100907 (Sanofi-Aventis, France), HY 10275 (Eli Lilly), APD 125 (Arena Pharmaceuticals, San Diego, CA), AVE8488 (Sanofi-Aventis, France), repinotan, sarizotan, eptapirone, buspirone, MN-305 (MediciNova, San Diego, CA), melatonin, ramelteon (ROZEREM®, Takeda Pharmaceuticals, Japan), VEC-162 (Vanda Pharmaceuticals, Rockville, MD), PD-6735 (Phase II Discovery), agomelatine, lamotrigine, gabapentin, pregabalin, orexin, a 1,3-biarylurea, SB-334867-a (GlaxoSmithKline, UK), GW649868 (GlaxoSmithKline), a benzamide derivative, Org 50081 (Organon-Netherlands), ritanserin, nefazodone, serzone, trazodone, Casopitant (GlaxoSmithKline), amitriptyline, amoxapine, bupropion, citalopram, clomipramine, desipramine, doxepin, duloxetine, escitalopram, fluoxetine, fluvoxamine, imipramine, isocarboxazid, maprotiline, mirtazapine, nefazodone, nortriptyline, paroxetine, phenelazine sulfate, protriptyline, sertraline, tranylcypromine, trazodone, trimipramine, venlafaxine, chlorpromazine, haloperidol, droperidol, fluphenazine, loxapine, mesoridazine molindone, perphenazine, pimozide, prochlorperazine promazine, thioridazine, thiothixene, trifluoperazine, clozapine, brexpiprazole, cariprazine, asenapine, lurasidone, aripiprazole, olanzapine, quetiapine, risperidone, ziprasidone and paliperidone; In addition to the therapeutic agents listed herewith, Method I-A or II-A, is further selected from pimavanserin (ACP-103) and pizotifen;

9.24 Method I-A or II-A wherein the therapeutic agent is an H3 agonist;

9.25 Method I-A or II-A, wherein the therapeutic agent is an H3 antagonist;

9.26 Method I-A or II-A, wherein the therapeutic agent is a noradrenergic agonist or antagonist;

9.27 Method I-A or II-A, wherein the therapeutic agent is a galanin agonist;

9.28 Method I-A or II-A, wherein the therapeutic agent is a CRH antagonist;

9.29 Method I-A or II-A, wherein the therapeutic agent is a human growth hormone;

9.30 Method I-A or II-A, wherein the therapeutic agent is a growth hormone agonist;

9.31 Method I-A or II-A, wherein the therapeutic agent is estrogen or an estrogen agonist;

9.32 Method I-A or II-A, wherein the therapeutic agent is $5\text{-HT}_6$ receptor antagonist;

9.33 Method I-A or II-A, wherein the therapeutic agent is a neurokinin-1 drug;

9.34 Method I-A or II-A, wherein a therapeutic agent is combined with compounds of Formula (I) and the therapeutic agent is an anti-Parkinson agent such as L-dopa, co-careldopa, duodopa, stalova, Symmetrel, benzotropine, biperiden, bromocryiptine, entacapone, pergolide, pramipexole, procyclidine, ropinirole, selegiline and tolcapone;

9.35 Method I-A or II-A, wherein compounds of Formula (I) may be used to treat sleep disorders, depression, psychosis, or any combinations thereof, in patients suffering from the listed diseases and/or Parkinson's disease;

9.36 Method I-A or II-A, wherein the disorder is selected from at least one or more of psychosis, e.g., schizophrenia, depression, mood disorders, sleep disorders (e.g., sleep maintenance and/or sleep onset) or any combination of disorders thereof;

9.37 Any of the foregoing methods wherein the disorder is sleep disorder;

9.38 Any of the foregoing methods, wherein the disorder is sleep disorder associated with psychosis, e.g., schizophrenia or Parkinson's disease; in free or pharmaceutically acceptable salt form.

In another embodiment of the sixth aspect, the current invention provides Method $I_P$ or Method II as hereinbefore described, wherein the method further comprises the administration to the patient of one or more therapeutic agents selected from compounds that modulate GABA activity (e.g., enhances the activity and facilitates GABA transmission), a GABA-B agonist, a 5-HT modulator (e.g., a $5\text{-HT}_{1A}$ agonist, a $5\text{-HT}_{2A}$ antagonist, a $5\text{-HT}_{2A}$ inverse agonist, etc.), a melatonin agonist, an ion channel modulator (e.g., blocker), a serotonin-2 receptor antagonist/reuptake inhibitor (a compound having both $5\text{-HT}_2$ antagonism and serotonin reuptake inhibition, i.e., SARIs), an orexin receptor antagonist, an H3 agonist or antagonist, a noradrenergic agonist or antagonist, a galanin agonist, a CRH antagonist, human growth hormone, a growth hormone agonist, estrogen, an estrogen agonist, a neurokinin-1 drug, an anti-depressant, and an antipsychotic agent, e.g., an atypical antipsychotic agent, in free or pharmaceutically acceptable salt form (Method $I_P$-A and II-A respectively). In a further embodiment of this aspect, the invention provides Method $I_P$-A or II-A as similarly described in any one of formulae 9.1-9.38.

In still another embodiment of the sixth aspect, Method $I_P$ or Method II as hereinbefore described further comprises the administration to the patient of one or more therapeutic agents selected from a cholinesterase inhibitor (e.g., acetylcholinesterase inhibitor) or an N-Methyl D-Aspartate (NMDA) receptor antagonist, in free or pharmaceutically acceptable salt form. In a specific embodiment, the cholinesterase inhibitor (e.g., acetylcholinesterase inhibitor) is selected from the group consisting of Tacrine, rivastigmine (Exelon), donepezil (Aricept), and galantamine (Razadyne, formerly called Reminyl)) in free or pharmaceutically acceptable salt form. In a further embodiment, the cholinesterase inhibitor (e.g., acetylcholinesterase inhibitor) is donepezil in free or pharmaceutically acceptable salt form. In another embodiment, the NMDA receptor antagonist is memantine in free or pharmaceutically acceptable salt form.

In a seventh aspect of the invention, the combination of a Compound of the Invention (e.g., any of Compounds I-IV and 1.1-1.10) and one or more second therapeutic agents as described in Methods I-A, II-A or any of 9.1-9.38, may be administered as a Pharmaceutical Composition or a depot Composition as hereinbefore described (e.g., Pharmaceutical Composition 2 or 2.1-2.4 or P.1-P.7). Similarly, the combination of a Compound of the Invention and one or more second therapeutic agents as described in Methods $I_p$-A, II-A or any of 9.1-9.38, may be administered as a Pharmaceutical Composition or a depot Composition as hereinbefore described. The combination compositions can include mixtures of the combined drugs, as well as two or more separate compositions of the drugs, which individual compositions can be, for example, co-administered together to a patient.

In a particular embodiment, Methods I-A, II-A, $I_p$-A, II-A or any of 9.1-9.38 comprises administering to a patient in need thereof, a Compound of the Invention in combination with an atypical antipsychotic agent, e.g., a compound selected from brexpiprazole, cariprazine, asenapine, lurasidone, clozapine, aripiprazole, olanzapine, quetiapine, risperidone, ziprasidone, or paliperidone, in free or pharmaceutically acceptable salt form, for example wherein the dosage of the atypical antipsychotic agent is reduced and/or side effects are reduced.

In another embodiment, Methods I-A, II-A, Methods $I_p$-A, II-A or any of 9.1-9.38 comprises administering to a patient in need thereof, a Compound of the Invention in combination with an anti-depressant, e.g., amitriptyline, amoxapine, bupropion, citalopram, clomipramine, desipramine, doxepin, duloxetine, escitalopram, fluoxetine, fluvoxamine, imipramine, isocarboxazid, maprotiline, mirtazapine, nefazodone, nortriptyline, paroxetine, phenelazine sulfate, protriptyline, sertraline, tranylcypromine, trazodone, trimipramine, or venlafaxine, in free or pharmaceutically acceptable salt form. Alternatively, the anti-depressant may be used as an adjunct medication in addition to the compounds of the Invention.

In still another embodiment, Methods I-A, II-A, $I_p$-A, II-A or any of 9.1-9.38 comprises administering to a patient in need thereof, a Compound of the Invention in combination with a compound that modulates GABA activity, e.g., a compound selected from doxepin, alprazolam, bromazepam, clobazam, clonazepam, clorazepate, diazepam, flunitrazepam, flurazepam, lorazepam, midazolam, nitrazepam, oxazepam, temazapam, triazolam, indiplon, zopiclone, eszopiclone, zaleplon, Zolpidem, gabaxadol, vigabatrin, tiagabine, EVT 201 (Evotec Pharmaceuticals), estazolam or any combinations thereof, in free or pharmaceutically acceptable salt form.

In another particular embodiment, Methods I-A, II-A, $I_p$-A, II-A or any of 9.1-9.38 comprises administering to a patient in need thereof, a Compound of the Invention in combination with doxepin in free or pharmaceutically acceptable salt form. Dosages of doxepin can vary in any range known to a person of ordinary skill in the art. In one example, a 10 mg dose of doxepin may be combined with any dosage of a compound of the Invention.

In another embodiment, Methods I-A, II-A, $I_p$-A, II-A or any of 9.1-9.38 comprises administering to a patient in need thereof, a Compound of the Invention in combination (including as part of a daily dosage regimen) with an atypical stimulant, e.g., a modafinil, adrafinil, or armodafinil. A regimen incorporating a Compound of the Invention with such drugs promotes more regular sleep, and avoids side effects such as psychosis or mania associated with higher levels of such drugs, e.g., in the treatment of bipolar depression, cognition associated with schizophrenia, and excessive sleepiness and fatigue in conditions such as Parkinson's disease and cancer.

In an eighth aspect, the invention provides use of a compound as described in the following formulae:

11.1 Compound of Formula I-IV or any of formulae 1-1.10, in free or pharmaceutically acceptable salt form;

11.2 a Pharmaceutical Composition as hereinbefore described (e.g., Pharmaceutical Composition 2 or 2.1-2.4 or P.1-P.7);

11.3 Depot Composition as hereinbefore described; or 11.4 Osmotic-controlled Release Oral Delivery System Composition as hereinbefore described, (in the manufacture of a medicament) for the treatment or prophylaxis of one or more disorders as disclosed hereinbefore, e.g., in any of Method I, any of 7.1-7.32, Method II, any of 8.1-8.8, Methods I-A, II-A, any of 9.1-9.38, Method $I_P$, Methods $I_P$-A, or any methods described in the sixth or seventh aspect of the invention.

In a ninth aspect, the invention provides a pharmaceutical composition as hereinbefore described, e.g., in the following formulae:

12.1 a Pharmaceutical Composition as hereinbefore described;

12.2 Depot Composition as hereinbefore described; or 12.3 Osmotic-controlled Release Oral delivery System Composition as hereinbefore described, for use in the treatment or prophylaxis of one or more disorders as disclosed hereinbefore, e.g., in any of Method I, any of 7.1-7.32, Method II, any of 8.1-8.8, Methods I-A, II-A, any of 9.1-9.38, Method $I_P$, Methods $I_P$-A, or any methods described in the sixth or seventh aspect of the invention.

In particular embodiments of any of the methods hereinbefore described, including any preceding embodiments of the fourth aspect (including Method I and any of Methods 7.1-7.32), the fifth aspect (including Method II and any of Methods 8.1-8.8), Method $I_P$, Methods $I_P$-A, the sixth aspect (including Method I-A, II-A and any of Methods 9.1-9.38), and the seventh aspect, the disorders and conditions referred to have their meaning as defined in the American Psychiatric Association's Diagnostic and Statistical Manual of Mental Disorders, Fifth Edition (DSM-V) (2013).

In other particular embodiments of any of the methods hereinbefore described, including any preceding embodiments of the fourth aspect (including Method I and any of Methods 7.1-7.32), the fifth aspect (including Method II and any of Methods 8.1-8.8), Method $I_P$, Methods $I_P$-A, the sixth aspect (including Method I-A, II-A and any of Methods 9.1-9.38), and the seventh aspect, the disorders and conditions referred to have their meaning as defined in the World Health Organization's International Classification of Diseases, Tenth Revision (ICD-10), Chapter V (Mental and Behavioral Disorders) (1992).

DETAILED DESCRIPTION OF THE INVENTION

If not otherwise specified or clear from context, the following terms as used herein have the following meanings.

"Residual symptoms" as used herein include negative symptoms and general psychopathology symptoms as described in the Positive and Negative Symptom Scale (PANSS) for Schizophrenia described in Kay et al., *Schizophr. Bull.* (1987) 13 (2):261-276, the contents of which are incorporated by reference in their entirety. Negative symptoms include: blunted affect, emotional withdrawal, poor rapport, passive/apathetic social withdrawal, difficulty in abstract thinking, lack of spontaneity and flow of conversation and stereotyped thinking General psychopathology symptoms include: somatic concern, anxiety, guilt feelings, tension, mannerisms and posturing, depression, motor retardation, uncooperativeness, unusual thought content, disorientation, poor attention, lack of judgment and insight, disturbance of volition, poor impulse control, preoccupation and active social avoidance. Residual symptoms may also include depression, cognitive impairment and sleep disorders (e.g., insomnia). Of these residual symptoms, the compounds of the invention are particularly useful for the treatment of passive social withdrawal, stereotyped thinking, somatic concerns, anxiety, tension, active social avoidance and depression. Therefore, the compounds of the present invention are particularly useful in improving social integration and social function in patients suffering from schizophrenia. Treatment of these residual symptoms is also particularly effective in schizophrenic patients also suffering from depression.

Unless otherwise indicated, the Compounds of the Invention, e.g., a compound of Formulas Ito IV or 1.1-1.10, may exist in free or salt, e.g., as acid addition salts, form. An acid-addition salt of a compound of the invention which is sufficiently basic, for example, an acid-addition salt with, for example, an inorganic or organic acid. In a particular embodiment, the salt of the Compounds of the Invention is a toluenesulfonic acid addition salt.

The Compounds of the Invention are intended for use as pharmaceuticals, therefore pharmaceutically acceptable salts are preferred. Salts which are unsuitable for pharmaceutical uses may be useful, for example, for the isolation or purification of free Compounds of the Invention, and are therefore also included.

Without being bound by theory, the current invention provides compounds which specifically limit, slow, alter and/or prevent the metabolism which has been found to occur in animals treated with the compounds such as the Compound Q:

Formula Q

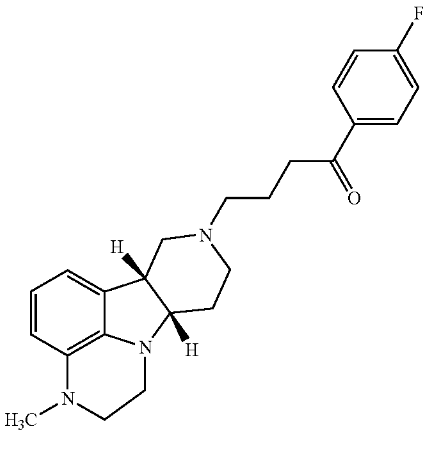

Due to the very similar chemical and physical properties of deuterium ($^2H$) atoms compared to normal hydrogen atoms ($^1H$), e.g., atomic charge, atomic volume, polarity, valency, etc., drug compounds in which deuterium is substituted for hydrogen are believed to generally have similar biological activity to the non-deuterated analog, but potentially with improved pharmacokinetic properties. It is particularly important that while deuterium atoms have almost double the atomic mass of protium atoms, their space volume and charge distribution are similar, these latter factors being critical in binding to biological molecules. Improved pharmacokinetic properties results from the significantly higher bond strength of a C-D bond compared to an H-D bond, and consequently, the higher energy barrier to D/H abstraction during an enzymatic (metabolic) reaction (the kinetic isotope effect). The extent to which such a substitution will result in an improvement of pharmacokinetic properties without a too severe loss in pharmacologic activity is variable. Thus, in some circumstances, the resulting deuterated compound only a moderate increase in pharmacokinetic stability, while in other circumstances, the resulting deuterated compound may have significantly improved stability. Moreover, it may be difficult to predict with certainty the effects of simultaneous deuterium substitutions. These may or may not result in additive (synergistic) improvement in metabolic stability.

Although many deuterated pharmaceutical compounds have been proposed and explored to date, only one deuterated pharmaceutical compound has been approved by the U.S. Food and Drug Administration, deutetrabenazine (Teva Pharmaceuticals, April 2017), a deuterated version of the Huntington's disease drug tetrabenazine, which has a therapeutically useful longer half-life than its non-deuterated counterpart.

The current disclosure provides compounds containing deuterium atoms at specific selected positions of the structure of the compound of Formula Q. These particular deuterations are expected to have in impact on metabolic degradation and clearance of said compounds because of their relationship to enzymatic pathways determined by the inventors to likely affect these compounds. These novel compounds are therefore expected to antagonize 5-$HT_{2A}$ receptors, inhibit the serotonin re-uptake transporter, and modulate dopaminergic protein phosphorylation, in a like manner as to their natural hydrogen analogs, yet with unexpectedly improved metabolic stability and pharmacokinetic properties.

The Compound of Formula Q have been showed to have a variety of useful pharmaceutical properties, each of which is expected to be shared by the compounds of the present disclosure. For example, the compound of Formula Q has potent 5-$HT_{2A}$, $D_1$ and/or $D_2$ modulation, and SERT antagonism.

The Compounds of the Invention may comprise one or more chiral carbon atoms. The compounds thus exist in individual isomeric, e.g., enantiomeric or diastereomeric form or as mixtures of individual forms, e.g., racemic/diastereomeric mixtures. Any isomer may be present in which the asymmetric center is in the (R)-, (S)-, or (R,S)-configuration. The invention is to be understood as embracing both individual optically active isomers as well as mixtures (e.g., racemic/diastereomeric mixtures) thereof. Accordingly, the Compounds of the Invention may be a racemic mixture or it may be predominantly, e.g., in pure, or substantially pure, isomeric form, e.g., greater than 70% enantiomeric/diastereomeric excess ("ee"), preferably greater than 80% ee, more preferably greater than 90% ee, most preferably greater than 95% ee. The purification of said isomers and the separation of said isomeric mixtures may be accomplished by standard techniques known in the art (e.g., column chromatography, preparative TLC, preparative HPLC, simulated moving bed and the like).

Geometric isomers by nature of substituents about a double bond or a ring may be present in cis (Z) or trans (E) form, and both isomeric forms are encompassed within the scope of this invention.

Alternatively and/or additionally, the Compounds of the Invention may be included as a depot formulation, e.g., by dispersing, dissolving or encapsulating the Compounds of the Invention in a polymeric matrix as described in the second and third aspect, such that the Compound is continually released as the polymer degrades over time. The release of the Compounds of the Invention from the polymeric matrix provides for the controlled- and/or delayed- and/or sustained-release of the Compounds, e.g., from the pharmaceutical depot composition, into a subject, for example a warm-blooded animal such as man, to which the pharmaceutical depot is administered. Thus, the pharmaceutical depot delivers the Compounds of the Invention to the subject at concentrations effective for treatment of the particular disease or medical condition over a sustained period of time, e.g., 14-180 days, preferably about 30, about 60 or about 90 days.

Polymers useful for the polymeric matrix in the Composition of the Invention (e.g., Depot composition of the Invention) may include a polyester of a hydroxy-fatty acid and derivatives thereof or other agents such as polylactic acid, polyglycolic acid, polycitric acid, polymalic acid, poly-beta.-hydroxybutyric acid, epsilon.-capro-lactone ring opening polymer, lactic acid-glycolic acid copolymer, 2-hydroxybutyric acid-glycolic acid copolymer, polylactic acid-polyethylene glycol copolymer or polyglycolic acid-polyethylene glycol copolymer), a polymer of an alkyl alpha-cyanoacrylate (for example poly(butyl 2-cyanoacrylate)), a polyalkylene oxalate (for example polytrimethylene oxalate or polytetramethylene oxalate), a polyortho ester, a polycarbonate (for example polyethylene carbonate or polyethylenepropylene carbonate), a polyortho-carbonate, a polyamino acid (for example poly-gamma.-L-alanine, poly-.gamma.-benzyl-L-glutamic acid or poly-y-methyl-L-glutamic acid), a hyaluronic acid ester, and the like, and one or more of these polymers can be used.

If the polymers are copolymers, they may be any of random, block and/or graft copolymers. When the above alpha-hydroxycarboxylic acids, hydroxydicarboxylic acids and hydroxytricarboxylic acids have optical activity in their molecules, any one of D-isomers, L-isomers and/or DL-isomers may be used. Among others, alpha-hydroxycarboxylic acid polymer (preferably lactic acid-glycolic acid polymer), its ester, poly-alpha-cyanoacrylic acid esters, etc. may be used, and lactic acid-glycolic acid copolymer (also referred to as poly(lactide-alpha-glycolide) or poly(lactic-co-glycolic acid), and hereinafter referred to as PLGA) are preferred. Thus, in one aspect the polymer useful for the polymeric matrix is PLGA. As used herein, the term PLGA includes polymers of lactic acid (also referred to as polylactide, poly (lactic acid), or PLA). Most preferably, the polymer is the biodegradable poly(d,l-lactide-co-glycolide) polymer.

In a preferred embodiment, the polymeric matrix of the invention is a biocompatible and biodegradable polymeric material. The term "biocompatible" is defined as a polymeric material that is not toxic, is not carcinogenic, and does not significantly induce inflammation in body tissues. The matrix material should be biodegradable wherein the polymeric material should degrade by bodily processes to products readily disposable by the body and should not accumulate in the body. The products of the biodegradation should also be biocompatible with the body in that the polymeric matrix is biocompatible with the body. Particular useful examples of polymeric matrix materials include poly (glycolic acid), poly-D,L-lactic acid, poly-L-lactic acid, copolymers of the foregoing, poly(aliphatic carboxylic acids), copolyoxalates, polycaprolactone, polydioxonone, poly(ortho carbonates), poly(acetals), poly(lactic acid-caprolactone), polyorthoesters, poly(glycolic acid-caprolactone), polyanhydrides, and natural polymers including albumin, casein, and waxes, such as, glycerol mono- and distearate, and the like. The preferred polymer for use in the practice of this invention is dl-(polylactide-co-glycolide). It is preferred that the molar ratio of lactide to glycolide in such a copolymer be in the range of from about 75:25 to 50:50.

Useful PLGA polymers may have a weight-average molecular weight of from about 5,000 to 500,000 daltons, preferably about 150,000 daltons. Dependent on the rate of degradation to be achieved, different molecular weight of polymers may be used. For a diffusional mechanism of drug release, the polymer should remain intact until all of the drug is released from the polymeric matrix and then degrade. The drug can also be released from the polymeric matrix as the polymeric excipient bioerodes.

The PLGA may be prepared by any conventional method, or may be commercially available. For example, PLGA can be produced by ring-opening polymerization with a suitable catalyst from cyclic lactide, glycolide, etc. (see EP-0058481B2; Effects of polymerization variables on PLGA properties: molecular weight, composition and chain structure).

It is believed that PLGA is biodegradable by means of the degradation of the entire solid polymer composition, due to the break-down of hydrolysable and enzymatically cleavable ester linkages under biological conditions (for example in the presence of water and biological enzymes found in tissues of warm-blooded animals such as humans) to form lactic acid and glycolic acid. Both lactic acid and glycolic acid are water-soluble, non-toxic products of normal metabolism, which may further biodegrade to form carbon dioxide and water. In other words, PLGA is believed to degrade by means of hydrolysis of its ester groups in the presence of water, for example in the body of a warm-blooded animal such as man, to produce lactic acid and glycolic acid and create the acidic microclimate. Lactic and glycolic acid are by-products of various metabolic pathways in the body of a warm-blooded animal such as man under normal physiological conditions and therefore are well tolerated and produce minimal systemic toxicity.

In another embodiment, the polymeric matrix useful for the invention may comprise a star polymer wherein the structure of the polyester is star-shaped. These polyesters have a single polyol residue as a central moiety surrounded by acid residue chains. The polyol moiety may be, e. g., glucose or, e. g., mannitol. These esters are known and described in GB 2,145,422 and in U.S. Pat. No. 5,538,739, the contents of which are incorporated by reference.

The star polymers may be prepared using polyhydroxy compounds, e. g., polyol, e.g., glucose or mannitol as the initiator. The polyol contains at least 3 hydroxy groups and has a molecular weight of up to about 20,000 Daltons, with at least 1, preferably at least 2, e.g., as a mean 3 of the hydroxy groups of the polyol being in the form of ester groups, which contain polylactide or co-polylactide chains. The branched polyesters, e.g., poly (d,l-lactide-co-glycolide) have a central glucose moiety having rays of linear polylactide chains.

The depot composition of the invention as hereinbefore described may comprise the polymer in the form of microparticles or nanoparticles, or in a liquid form, with the Compounds of the Invention dispersed or encapsulated therein. "Microparticles" is meant solid particles that contain the Compounds of the Invention either in solution or in solid form wherein such compound is dispersed or dissolved within the polymer that serves as the matrix of the particle. By an appropriate selection of polymeric materials, a microparticle formulation can be made in which the resulting microparticles exhibit both diffusional release and biodegradation release properties.

In a particular embodiment, the Compound of the Invention is formulated into microparticles of an appropriate size to allow slow release kinetics after intramuscular injection.

When the polymer is in the form of microparticles, the microparticles may be prepared using any appropriate method, such as by a solvent evaporation or solvent extraction method. For example, in the solvent evaporation method, the Compounds of the Invention and the polymer may be dissolved in a volatile organic solvent (for example a ketone such as acetone, a halogenated hydrocarbon such as chloroform or methylene chloride, a halogenated aromatic hydrocarbon, a cyclic ether such as dioxane, an ester such as ethyl acetate, a nitrile such as acetonitrile, or an alcohol such as ethanol) and dispersed in an aqueous phase containing a suitable emulsion stabilizer (for example polyvinyl alcohol, PVA). The organic solvent is then evaporated to provide microparticles with the Compounds of the Invention encapsulated therein. In the solvent extraction method, the Compounds of the Invention and polymer may be dissolved in a polar solvent (such as acetonitrile, dichloromethane, methanol, ethyl acetate or methyl formate) and then dispersed in an aqueous phase (such as a water/PVA solution). An emulsion is produced to provide microparticles with the Compounds of the Invention encapsulated therein. Spray drying is an alternative manufacturing technique for preparing the microparticles.

Another method for preparing the microparticles of the invention is also described in both U.S. Pat. Nos. 4,389,330 and 4,530,840, the contents of which are incorporated by reference.

The microparticle of the present invention can be prepared by any method capable of producing microparticles in a size range acceptable for use in an injectable composition. One preferred method of preparation is that described in U.S. Pat. No. 4,389,330. In this method the active agent is dissolved or dispersed in an appropriate solvent. To the agent-containing medium is added the polymeric matrix material in an amount relative to the active ingredient that provides a product having the desired loading of active agent. Optionally, all of the ingredients of the microparticle product can be blended in the solvent medium together.

Solvents for the Compounds of the Invention and the polymeric matrix material that can be employed in the practice of the present invention include organic solvents, such as acetone; halogenated hydrocarbons, such as chloroform, methylene chloride, and the like; aromatic hydrocarbon compounds; halogenated aromatic hydrocarbon compounds; cyclic ethers; alcohols, such as, benzyl alcohol; ethyl acetate; and the like. In one embodiment, the solvent for use in the practice of the present invention may be a mixture of benzyl alcohol and ethyl acetate. Further information for the preparation of microparticles useful for the invention can be found in U.S. Patent Publication Number 2008/0069885, the contents of which are incorporated herein by reference in their entirety.

The amount of the Compounds of the Invention incorporated in the microparticles usually ranges from about 1 wt % to about 90 wt. %, preferably 30 to 50 wt. %, more preferably 35 to 40 wt. %. By weight % is meant parts of the Compounds of the Invention per total weight of microparticle.

The pharmaceutical depot may comprise a pharmaceutically-acceptable diluent or carrier, such as a water miscible diluent or carrier.

Details of Osmotic-controlled Release Oral Delivery System composition may be found in EP 1 539 115 (U.S. Pub. No. 2009/0202631) and WO 2000/35419, the contents of each of which are incorporated by reference in their entirety.

A "therapeutically effective amount" is any amount of the Compounds of the invention (for example as contained in the pharmaceutical depot) which, when administered to a subject suffering from a disease or disorder, is effective to cause a reduction, remission, or regression of the disease or disorder over the period of time as intended for the treatment.

Dosages employed in practicing the present invention will of course vary depending, e.g. on the particular disease or condition to be treated, the particular Compounds of the Invention used, the mode of administration, and the therapy desired.

Compounds of the Invention may be administered by any satisfactory route, including orally, parenterally (intravenously, intramuscular or subcutaneous) or transdermally, but are preferably administered orally. In certain embodiments, the Compounds of the Invention, e.g., in depot formulation, is preferably administered parenterally, e.g., by injection.

In general, satisfactory results for Method I or any of formulae 7.1-7.32 or Method $I_P$ or use of the Compounds of the Invention as hereinbefore described, e.g. for the treatment of a combination of diseases such as a combination of at least depression, psychosis, e.g., (1) psychosis, e.g., schizophrenia, in a patient suffering from depression; (2) depression in a patient suffering from psychosis, e.g., schizophrenia; (3) mood disorders associated with psychosis, e.g., schizophrenia, or Parkinson's disease; and (4) sleep disorders associated with psychosis, e.g., schizophrenia, or Parkinson's disease, as set forth above are indicated to be obtained on oral administration at dosages of the order from about 1 mg to 100 mg once daily, preferably about 2.5 mg-50 mg, e.g., 2.5 mg, 5 mg, 10 mg, 20 mg, 30 mg, 40 mg or 50 mg, once daily, preferably via oral administration.

Satisfactory results for Method II or any of 8.1-8.8, Method II or use of the Compounds of the Invention as hereinbefore described, e.g. for the treatment of sleep disorder alone or agitation, aggressive behaviors, post-traumatic stress disorder or impulse control disorder alone, e.g., intermittent explosive disorder alone are indicated to be obtained on oral administration at dosages of the order from about 1 mg-10 mg once daily, e.g., about 2.5 mg-5 mg, e.g., 2.5 mg, 3 mg, 4 mg, 5 mg or 10 mg, of a Compound of the Invention, in free or pharmaceutically acceptable salt form, once daily, preferably via oral administration.

Satisfactory results for Method I-A or any of 9.1-9.38 or Method $I_P$-A are indicated to be obtained at less than 100 mg, preferably less than 50 mg, e.g., less than 40 mg, less than 30 mg, less than 20 mg, less than 10 mg, less than 5 mg, less than 2.5 mg, once daily. Satisfactory results for Method II-A or any of 9.1-9.38 are indicated to be obtained at less than 10 mg, e.g., less than 5 mg or, preferably less than 2.5 mg.

For treatment of the disorders disclosed herein wherein the depot composition is used to achieve longer duration of action, the dosages will be higher relative to the shorter action composition, e.g., higher than 1-100 mg, e.g., 25 mg, 50 mg, 100 mg, 500 mg, 1,000 mg, or greater than 1000 mg. In a particular embodiment, the dosage regimen for depot composition includes an initial oral immediate dose along with depot release so as to provide a steady-state blood level of the drug. Duration of action of the Compounds of the Invention may be controlled by manipulation of the polymer composition, i.e., the polymer:drug ratio and microparticle size. Wherein the composition of the invention is a depot composition, administration by injection is preferred.

The pharmaceutically acceptable salts of the Compounds of the Invention can be synthesized from the parent compound which contains a basic or acidic moiety by conventional chemical methods. Generally, such salts can be prepared by reacting the free base forms of these compounds with a stoichiometric amount of the appropriate acid in water or in an organic solvent, or in a mixture of the two; generally, non-aqueous media like ether, ethyl acetate, ethanol, isopropanol, or acetonitrile are preferred. Further details for the preparation of these salts, e.g., toluenesulfonic salt in amorphous or crystal form, may be found in PCT/US08/03340 and/or U.S. Provisional Appl. No. 61/036,069 (and their equivalent, US 2011/112105).

Pharmaceutical compositions comprising Compounds of the Invention may be prepared using conventional diluents or excipients (an example include, but is not limited to sesame oil) and techniques known in the galenic art. Thus, oral dosage forms may include tablets, capsules, solutions, suspensions and the like.

All references herein to dosage, dosage rate or therapeutically effect amount of a Compound or Composition of the Invention refers to the equivalent free-base moiety in the dosage, excluding any salts.

Methods of Making the Compounds of the Invention

The intermediates of the Compounds of the Invention may generally be prepared as described in in PCT/US08/03340 (WO 2008/112280) or U.S. Pat. No. 8,309,722; U.S. application Ser. No. 10/786,935 and U.S. Pat. Nos. 7,081,455; 6,548,493; 7,238,690; 6,552,017; 6,713,471; 7,183,282; U.S. RE39680, and U.S. RE39679, and WO 2015/154025, the contents of each of which are incorporated by reference in their entirety. Salts of the Compounds of the Invention may also be prepared as similarly described in U.S. Pat. Nos. 6,548,493; 7,238,690; 6,552,017; 6,713,471; 7,183,282; U.S. RE39680; U.S. RE39679; and WO 2009/114181, the contents of each of which are incorporated by reference in their entirety.

Isolation or purification of the diastereomers of the Compounds of the Invention may be achieved by conventional methods known in the art, e.g., column purification, preparative thin layer chromatography, preparative HPLC, crystallization, trituration, simulated moving beds and the like.

Example 1

1-(4-fluorophenyl)-4-((6bR,10aS)-1,1,2,2-tetradeuterio-3-methyl-2,3,6b,7,10,10a-hexahydro-1H-pyrido[3',4':4,5]pyrrolo[1,2,3-de]quinoxalin-8(9H)-yl)butan-1-one p-toluenesulfonate

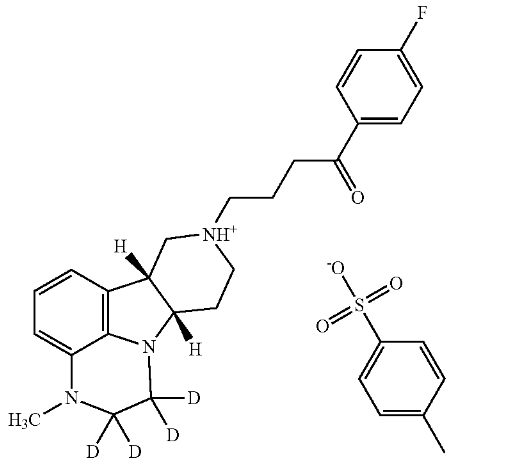

Step 1: To a degassed mixture of (4aS,9bR)-ethyl 6-bromo-3,4,4a,5-tetrahydro-1H-pyrido[4,3-b]indole-2(9bH)-carboxylate (1.60 g, 8.0 mmol), 2-chloro-2,2-dideuterio-N-methylacetamide (1.74 g, 16 mmol), and KI (2.68 g, 16 mmol) in dioxane (28 mL), diisopropylethylamine (2.8 mL, 16 mmol) is added at room temperature. The reaction mixture is then heated to 104° C. under vigorous stirring for 20 h. Solvents are removed under vacuum and the residue is suspended in dichloromethane (50 mL) and extracted with water (20 mL). The organic phase is separated, dried over $K_2CO_3$ and concentrated to a residue. The product is purified by silica gel column chromatography using a gradient of 0-100% mixed solvents [ethyl acetate/methanol (10:1 v/v)] in ethyl acetate to yield (4aS,9bR)-ethyl 6-bromo-5-(1,1-dideuterio-2-(methylamino)-2-oxoethyl)-3,4,4a,5-tetrahydro-1H-pyrido[4,3-b]indole-2(9bH)-carboxylate a brown solid (1.15 g, yield 36%). MS (ESI) m/z 398.1 $[M+1]^+$.

Step 2: To a degassed mixture of (4aS,9bR)-ethyl 6-bromo-5-(1,1-dideuterio-2-(methylamino)-2-oxoethyl)-3,4,4a,5-tetrahydro-1H-pyrido[4,3-b]indole-2(9bH)-carboxylate (1.0 g, 2.5 mmol), $K_2CO_3$ (760 mg, 5.5 mmol), CuI (120 mg, 0.63 mmol) in dioxane (10 mL), N,N,N',N'-tetramethylethlenediamine (0.23 mL, 1.5 mmol) is added at room temperature. The reaction mixture is then heated to 99° C. under vigorous stirring for 4 days. After cooling to room temperature, the mixture is directly loaded on a silica gel column. The product is purified by column chromatography using 100% ethyl acetate to obtain (6bR,10aS)-ethyl 1,1-dideuterio-3-methyl-2-oxo-2,3,6b,7,10,10a-hexahydro-1H-pyrido[3',4':4,5]pyrrolo[1,2,3-de]quinoxaline-8(9H)-carboxylate as a brown solid (210 mg, yield 11%). MS (ESI) m/z 318.2 $[M+1]^+$.

Step 3: To a dried flask, (6bR,10aS)-ethyl 1,1-dideuterio-3-methyl-2-oxo-2,3,6b,7,10,10a-hexahydro-1H-pyrido[3',4':4,5]pyrrolo[1,2,3-de]quinoxaline-8(9H)-carboxylate (210 mg, 0.66 mmol) is dissolved in THF (2.0 mL). $BD_3$ (1.0M in THF, 3.5 mL) is dropped in slowly to control temperature<30° C. The resulting mixture is stirred over night at room temperature and is then cooled with ice. MeOH-$d_4$ (2.0 mL) and $D_2O$ (1.0 mL) are added successively to quench the reaction. The solvents are removed under vacuum and the residue is suspended in dichloromethane (20 mL) and extracted with water (2.0 mL). The organic phase is separated and dried over $K_2CO_3$. The product is purified by silica gel column chromatography using a gradient of 0-40% ethyl acetate in hexanes mixed solvents to obtain (6bR,10aS)-ethyl 1,1,2,2-tetradeuterio-3-methyl-2,3,6b,7,10,10a-hexahydro-1H-pyrido[3',4':4,5]pyrrolo[1,2,3-de]quinoxaline-8(9H)-carboxylate as a colorless oil (81 mg, yield 40.5%). MS (ESI) m/z 306.2 $[M+1]^+$.

Step 4: To a degassed flask, (6bR,10aS)-ethyl 1,1,2,2-tetradeuterio-3-methyl-2,3,6b,7,10,10a-hexahydro-1H-pyrido[3',4':4,5]pyrrolo[1,2,3-de]quinoxaline-8(9H)-carboxylate (81 mg, 0.26 mmol) is suspended in HCl (37%, 3 mL). The mixture is heated at 99° C. for 24 h to give a clear solution. After cooling, the acidic solution is concentrated to leave a blue residue, which is in turn suspended in a mixture of dichloromethane (30 mL) and water (2 mL). The mixture is cooled with ice and NaOH (10N) is added slowly until pH>14. The organic phase is separated and dried over $K_2CO_3$. After concentrating, the crude product (≈30 mg) is used directly for the next step without further purification. MS (ESI) m/z 234.2 $[M+1]^+$.

Step 5: A mixture of (6bR,10aS)-1,1,2,2-tetradeuterio-3-methyl-2,3,6b,7,8,9,10,10a-octahydro-1H-pyrido[3',4':4,5]pyrrolo[1,2,3-de]quinoxaline (30 mg, 0.13 mmol), 4-chloro-4'-fluorobutyrophenone (53 μL, 0.32 mmol) and KI (59 mg, 0.35 mmol) in DMF (2 mL) is bubbled with argon for 3 minutes and then diisopropylethylamine (45 μL, 0.32 mmol) is added. The resulting mixture is heated to 76° C. and stirred at this temperature for 2 h. The solvent is removed and the residue is purified by silica gel column chromatography using a gradient of 0-100% mixed solvents [ethyl acetate/methanol/7N $NH_3$ (10:1:0.1 v/v)] in ethyl acetate to obtain 1-(4-fluorophenyl)-4-((6bR,10aS)-1,1,2,2-tetradeuterio-3-methyl-2,3,6b,7,10,10a-hexahydro-1H-pyrido[3',4':4,5]pyrrolo[1,2,3-de]quinoxalin-8(9H)-yl)butan-1-one as a brown oil (20 mg, yield 39%). MS (ESI) m/z 398.2 $[M+1]^+$.

Step 6: 1-(4-fluorophenyl)-4-((6bR,10aS)-1,1,2,2-tetradeuterio-3-methyl-2,3,6b,7,10,10a-hexahydro-1H-pyrido[3',4':4,5]pyrrolo[1,2,3-de]quinoxalin-8(9H)-yl)butan-1-one (18.63 mg, 0.047 mmol) is dissolved in 2-propanol (0.3 ml). p-Toluenesulfonic acid monohydrate (12.07 mg, 0.063 mmol) is dissolved in 2-propanol (0.3 ml). 0.2 mL of acid solution is dropped slowly into the d4-free base solution with strong stirring. The resulting clear solution is stirred for an additional 2 h at room temperature, during which a white solid gradually precipitates. The mixture is stored at −20° C. over the weekend and then the solid is recovered by filtration. The solid is rinsed with cold 2-propanol (0.5 ml) and dried over vacuum. About 20 mg product is obtained as a white solid. Yield 75%. $^1$HNMR (500 MHz, DMSO-$d_6$) δ 9.1 (s, 1H), 8.2-7.9 (m, 2H), 7.6-7.4 (m, 2H), 7.4-7.3 (m, 2H), 7.1 (dd, J=2.11, 7.29 Hz, 2H), 6.6 (td, J=1.86, 7.55, 8.02 Hz, 1H), 6.6-6.5 (m, 1H), 6.5-6.4 (m, 1H), 3.6 (dd, J=6.36, 12.18 Hz, 1H), 3.5 (d, J=13.09 Hz, 1H), 3.4-3.3 (m, 2H), 3.2 (d, J=4.64 Hz, 1H), 3.2-2.9 (m, 5H), 2.8 (s, 3H), 2.6 (q, J=11.67 Hz, 1H), 2.3 (s, 3H), 2.2-1.9 (m, 3H). MS (ESI) m/z 398.2 $[M+1]^+$ (for free base).

Example 2: Measurement of Parent and Metabolite Levels in Mice

The compound of Example 1 and the compound of Formula Q are co-dosed in mice (n=3), and the levels of the both compounds are studied. Procedures for the synthesis of the compound of Formula Q can be found in WO 2008/112280. After single dose oral administration of the test compounds, plasma and brain levels are measured at 0.25, 0.5, 1, 2, and 4 hours. The mean values for maximum concentration, time to maximum concentration, and Area Under the Curve (AUC) for both compounds is determined. The results are summarized in Table 1 below.

| | Plasma(ng/mL) | | Brain(ng/g) | |
|---|---|---|---|---|
| Time (hr) | F. Q | Ex. 1 | F. Q | Ex. 1 |
| 0.25 | 28.2 | 30.4 | 228.3 | 238.0 |
| 0.5 | 34.9 | 38.1 | 383.7 | 402.4 |
| 1 | 11.0 | 11.6 | 37.9 | 39.4 |
| 2 | 29.9 | 31.4 | 65.6 | 67.7 |
| 4 | 16.3 | 16.8 | 58.8 | 62.1 |
| Tmax (hr) | 0.5 | 0.5 | 0.5 | 0.5 |
| Cmax (ng/mL) | 34.9 | 38.1 | 383.7 | 402.4 |
| AUC (ng · hr/mL) | 89.5 | 94.5 | 386.6 | 403.6 |

It is found that the both plasma and blood concentrations of the compound of Example 1 are higher than the compound of Formula Q, resulting in both higher Cmax values and higher AUC values. This demonstrates reduced metabolic clearance of the tetra-deuterated compound of Example 1 compared to its non-deuterated counterpart, the compound of Formula Q.

Receptor binding studies indicate that the compound of Example 1 shows substantially the same receptor binding profile as the non-deuterated compound of Formula Q (including, e.g., serotonin receptor (e.g., 5-$HT_{2A}$), dopamine receptor (e.g., D2) and serotonin transporter binding).

The invention claimed is:

1. A compound of formula II,

Formula II

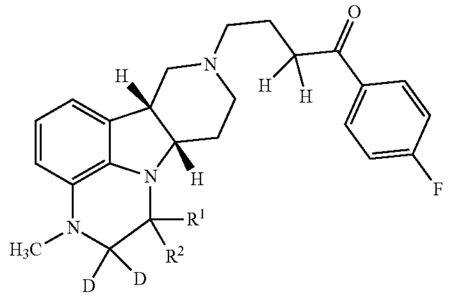

wherein $R^1$ and $R^2$ are both D, in solid mono-tosylate salt form.

2. The compound according to claim 1, wherein the compound has greater than 90% incorporation of deuterium at the indicated deuterium positions of the structure.

3. A pharmaceutical composition comprising the compound according to claim 1 in combination or association with a pharmaceutically acceptable diluent or carrier.

4. The compound according to claim 1, wherein the compound of Formula II is in crystalline form.

5. The compound according to claim 1, wherein the compound of Formula II is in amorphous form.

6. The compound according to claim 1, wherein the compound has greater than 95% incorporation of deuterium at the indicated deuterium positions of the structure.

7. The pharmaceutical composition according to claim 3, wherein the composition is a tablet or capsule.

8. The compound according to claim 4, wherein the compound has greater than 90% incorporation of deuterium at the indicated deuterium positions of the structure.

9. The compound according to claim 4, wherein the compound has greater than 95% incorporation of deuterium at the indicated deuterium positions of the structure.

10. A pharmaceutical composition comprising the compound according to claim 4 in combination or association with a pharmaceutically acceptable diluent or carrier.

11. The pharmaceutical composition according to claim 10, wherein the composition is a tablet or capsule.

12. The compound according to claim 5, wherein the compound has greater than 90% incorporation of deuterium at the indicated deuterium positions of the structure.

13. The compound according to claim 5, wherein the compound has greater than 95% incorporation of deuterium at the indicated deuterium positions of the structure.

14. A pharmaceutical composition comprising the compound according to claim 5 in combination or association with a pharmaceutically acceptable diluent or carrier.

15. The pharmaceutical composition according to claim 14, wherein the composition is a tablet or capsule.

* * * * *